US011578119B2

(12) United States Patent
Tkaczyk et al.

(10) Patent No.: US 11,578,119 B2
(45) Date of Patent: Feb. 14, 2023

(54) ANTIBODIES DIRECTED AGAINST *STAPHYLOCOCCUS AUREUS* LEUKOTOXINS

(71) Applicants: MedImmune, LLC, Gaithersburg, MD (US); Humabs BioMed SA, Bellinzona (CH)

(72) Inventors: Christine Tkaczyk, Gaithersburg, MD (US); Bret Sellman, Gaithersburg, MD (US); Qun Du, Gaithersburg, MD (US); Melissa Damschroder, Gaithersburg, MD (US); Davide Corti, Bellinzona (CH); Andrea Minola, Bellinzona (CH)

(73) Assignees: MedImmune LLC, Gaithersburg, MD (US); Humabs BioMed SA, Bellinzona (CH)

( * ) Notice: Subject to any disclaimer, the term of this patent is extended or adjusted under 35 U.S.C. 154(b) by 57 days.

(21) Appl. No.: 17/340,622

(22) Filed: Jun. 7, 2021

(65) Prior Publication Data
US 2021/0363229 A1 Nov. 25, 2021

Related U.S. Application Data

(62) Division of application No. 16/596,445, filed on Oct. 8, 2019, now Pat. No. 11,059,884.

(60) Provisional application No. 62/743,501, filed on Oct. 9, 2018.

(51) Int. Cl.
*C07K 16/12* (2006.01)
*A61P 31/04* (2006.01)
*G01N 33/569* (2006.01)

(52) U.S. Cl.
CPC .......... *C07K 16/1271* (2013.01); *A61P 31/04* (2018.01); *G01N 33/56938* (2013.01); *C07K 2317/41* (2013.01); *C07K 2317/51* (2013.01); *C07K 2317/515* (2013.01); *C07K 2317/565* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 9,527,905 | B2 | 12/2016 | Sellman et al. |
| 9,845,348 | B2 | 12/2017 | Sellman et al. |
| 9,879,070 | B2 | 1/2018 | Sellman et al. |
| 10,457,724 | B2 | 10/2019 | Sellman et al. |
| 10,730,934 | B2 | 8/2020 | Sellman et al. |
| 10,759,849 | B2 | 9/2020 | Sellman et al. |
| 11,059,884 | B2 | 7/2021 | Tkaczyk et al. |
| 2011/0274693 | A1 | 11/2011 | Torres et al. |
| 2017/0129943 | A1 | 5/2017 | Sellman et al. |
| 2019/0016787 | A1 | 1/2019 | Sellman et al. |
| 2019/0077851 | A1 | 3/2019 | Jafri et al. |
| 2020/0048330 | A1 | 2/2020 | Tkaczyk et al. |
| 2020/0109189 | A1 | 4/2020 | Tkaczyk et al. |
| 2020/0407429 | A1 | 12/2020 | Sellman et al. |

FOREIGN PATENT DOCUMENTS

| | | |
|---|---|---|
| WO | WO-2012109285 A2 | 8/2012 |
| WO | WO-2014074540 A2 | 5/2014 |
| WO | WO-2015055814 A1 | 4/2015 |
| WO | WO-2015175874 A2 | 11/2015 |
| WO | WO-2016166223 A1 | 10/2016 |
| WO | WO-2017075188 A2 | 5/2017 |
| WO | WO-2020023644 A2 | 1/2020 |
| WO | WO-2020076789 A2 | 4/2020 |
| WO | WO-2020076790 A1 | 4/2020 |

OTHER PUBLICATIONS

Adhikari, R.P., et al., "Antibodies to *S. aureus* Luks-PV Attenuated Subunit Vaccine Neutralize a Broad Spectrum of Canonical and Non-Canonical BiComponent Leukotoxin Pairs," PLOS ONE 10(9):e0137874, 17 pages, Public Library of Science, United States (2015).

Alonzo, F., et al., "Bacterial Survival Amidst an Immune Onslaught: The Contribution of the *Staphylococcus aureus* Leukotoxins," PLOS Pathogens 9(2):e1003143, 4 pages, Public Library of Science, United States (2013).

Cheung, Y.C., "The Potential use of toxin antibodies as a strategy for controlling acute *Staphylococcus aureus* infections," Expert Opinion on Therapeutic Targets 16(6):601-612, Informa Healthcare, United Kingdom (2012).

Digiandomenico, A and Sellman, B.R., "Antibacterial Monoclonal Antibodies: the Next Generation?," Current Opinion in Microbiology, 27:78-85, Current Biology, England (Oct. 2015).

Foletti, D., et al., "Mechanism of Action and In Vivo Efficacy of a Human-Derived Antibody against *Staphylococcus aureus* A-Hemolysin," Journal of Molecular Biology, 425(10):1641-1654, Elsevier, England (May 2013).

Hazenbos, W.L., et al., "Novel Staphylococcal Glycosyltransferases Sdga and Sdgb Mediate Immunogenicity and Protection of Virulence-associated Cell Wall Proteins," PLOS Pathogens, 9(10):e1003653, 18 pages, Public Library of Science, United States (2013).

Hua, L., et al., "Assessment of an Anti-Alpha-Toxin Monoclonal Antibody for Prevention and Treatment of *Staphylococcus aureus*-Induced Pneumonia," Antimicrobial Agents and Chemotherapy, 58(2):1108-1117, American Society for Microbiology, United States (2014).

International Search Report and Written Opinion in PCT/US2019/055144, dated Jan. 20, 2020, European Patent Office, Netherlands, 20 pages.

(Continued)

*Primary Examiner* — Brian Gangle
(74) *Attorney, Agent, or Firm* — Sterne, Kessler, Goldstein & Fox P.L.L.C.

(57) ABSTRACT

The present disclosure is directed to leukotoxin-binding antibodies and antigen-binding fragments thereof. The antibodies and fragments can be used, for example, to detect leukotoxin and/or in methods of treating and preventing *Staphylococcus aureus* infections.

20 Claims, 3 Drawing Sheets

Figure 1:
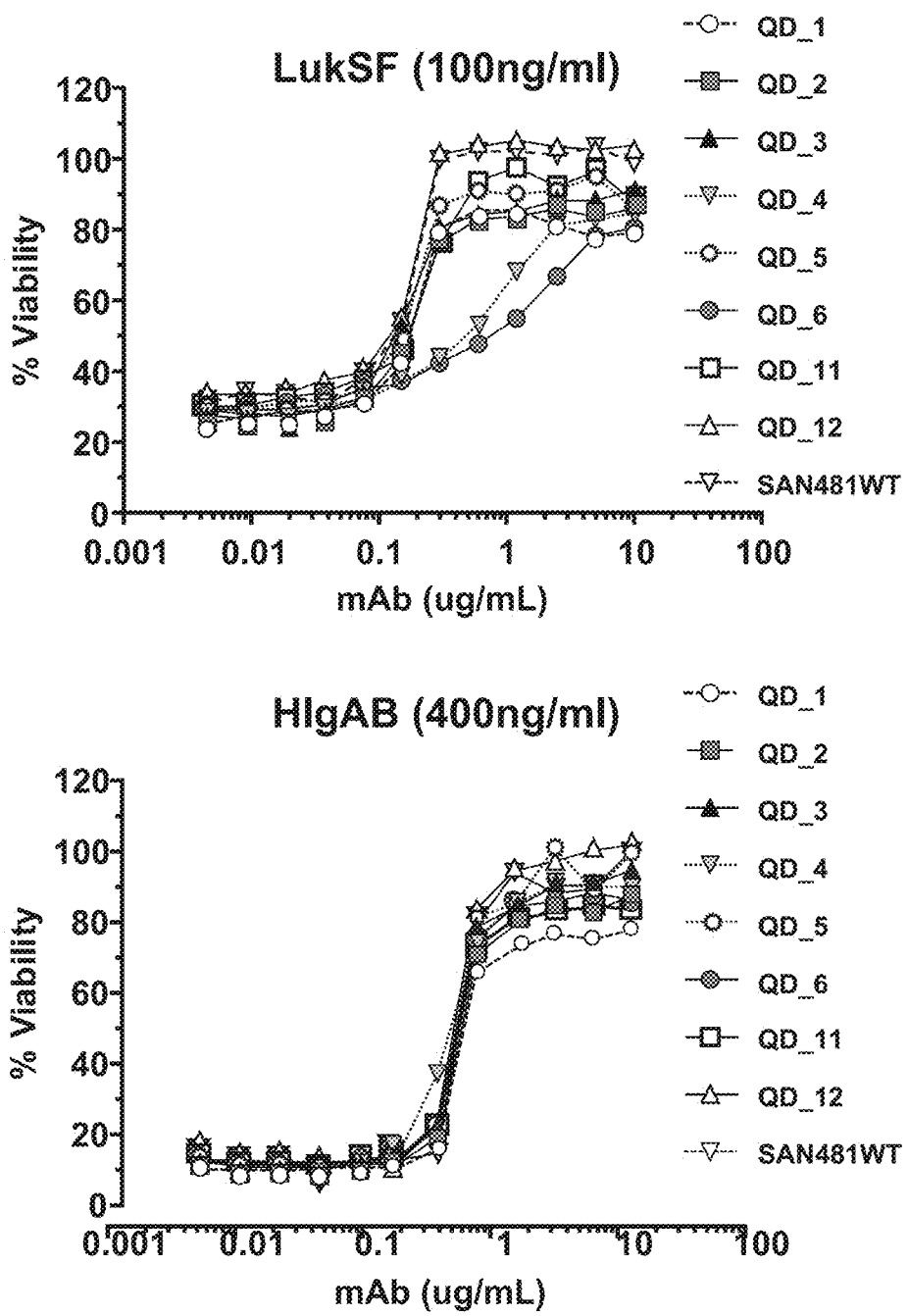

Specification includes a Sequence Listing.

(56) References Cited

OTHER PUBLICATIONS

Karauzum, H., et al., "Synthetic Human Monoclonal Antibodies toward Staphylococcal Enterotoxin B (Seb) Protective against Toxic Shock Syndrome," Journal of Biological Chemistry, 287(30):25203-25215, American Society for Biochemistry and Molecular Biology, United States (Jul. 2012).
Laventie, B.J., et al., "Heavy chain-only antibodies and tetravalent bispecific antibody neutralizing Staphylococcus aureus leukotoxins," Proceedings of the National Academy of Sciences, 108(39):16404-16409, United States National Academy of Sciences, United States (2011).
Lowy, F.D., "Staphylococcus aureus Infections," The New England Journal of Medicine, 339(8):520-532, Massachusetts Medical Society, United States (Aug. 1998).
Rouha, H., et al., "Five Birds, One Stone: Neutralization of A-hemolysin and 4 Bi-component Leukocidins of Staphylococcus aureus with a Single Human Monoclonal Antibody," MAbs, 7(1):243-254, Taylor & Francis, United States (2015).
Caldas, C., et al., "Humanization of the Anti-CD18 Antibody 6.7: An Unexpected Effect of a Framework Residue in Binding to Antigen," Molecular Immunology 39(15):941-952, Pergamon Press, United Kingdom (May 2003).
Casadevall, A and Janda, A., "Immunoglobulin Isotype Influences Affinity and Specificity," Proceedings of the National Academy of Sciences of the United States of America 109(31):12272-12273, National Academy of Sciences, United States (Jul. 2012).
Chien, N.C., et al., "Significant Structural and Functional Change of an Antigen-Binding Site by a Distant Amino Acid Substitution: Proposal of a Structural Mechanism," Proceedings of the National Academy of Sciences of the United States of America 86(14):5532-5536, National Academy of Sciences, United States (Jul. 1989).
Giusti, A.M., et al., "Somatic diversification of S107 from an antiphosphocholine to an anti-DNA autoantibody is due to a single base change in its heavy chain variable region," Proceedings of the National Academy of Sciences of the United States of America 84(9):2926-2930, National Academy of Sciences, United States (May 1987).
Gouaux, E., et al., "Alpha-Hemolysin, gamma-hemolysin, and leukocidin from Staphylococcus aureus: distant in sequence but similar in structure," Protein Science 6(12):2631-2635, Cold Spring Harbor Laboratory Press, United States (Dec. 1997).
Greenspan, N.S. and Di Cera, E., "Defining Epitopes: It's not as Easy as it Seems," Nature Biotechnology 17(10):936-937, Nature Publishing Group, United States (Oct. 1999).
Skolnick, J. and Fetrow, J., "From Genes to Protein Structure and Function: Novel Applications of Computational Approaches in the Genomic Era," Trends in Biotechnology 18:34-39, Elsevier Science Publishers, London (Jan. 2000).
Thomsen, I. P., et al., "Monoclonal Antibodies Against the Staphylococcus aureus Bicomponent Leukotoxin AB Isolated Following Invasive Human Infection Reveal Diverse Binding and Modes of Action," Journal of Infectious Diseases 215(7):1124-1131, Oxford University Press, United Kingdom (Apr. 2017).
Tkaczyk, C., et al., "Identification of anti-alpha toxin monoclonal antibodies that reduce the severity of Staphylococcus aureus dermonecrosis and exhibit a correlation between affinity and potency," Clin Vaccine Immunol 19(3):377-385, American Society for Microbiology, United States (Jan. 2012).
Tkaczyk, C., et al., "Targeting Alpha Toxin and ClfA with a Multimechanistic Monoclonal-Antibody-Based Approach for Prophylaxis of Serious Staphylococcus aureus Disease," mBio 7(3):e00528-16, 11 pages, American Society for Microbiology, United States (May-Jun. 2016).
Tkaczyk C., et al., "Multimechanistic Monoclonal Antibodies (MAbs) Targeting Staphylococcus aureus Alpha-Toxin and Clumping Factor A: Activity and Efficacy Comparisons of a MAb Combination and an Engineered Bispecific Antibody Approach," Antimicrobial Agents and Chemotherapy 61(8):e00629-17, 14 pages, American Society for Microbiology, United States (Aug. 2017).
Tkaczyk, C., "Antibacterial monoclonal antibodies: A strategy to prevent serious bacterial infections," presented at the Society for Laboratory Automation and Screening on Feb. 4, 2019, retrieved from the Internet: https://www.eventscribe.com/2019/SLAS2019/fsPopup.asp?efp=V0IVQUNFWIA2OTg4&PresentationID=466606&rnd=9.235436E-02&mode=presinfo on Jul. 15, 2020, 2 pages.
Winkler, K., et al., "Changing the Antigen Binding Specificity by Single Point Mutations of an Anti-p24 (HIV-1) Antibody," The Journal of Immunology 165(8):4505-4514, The American Association of Immunologists, United States (Oct. 2000).
Yanjie, M., et al., "713. Preventive Administration of MEDI6389, a Combination of Monoclonal Antibodies (mAbs) Targeting Alpha-Toxin (AT), Panton-Valentine Leukocidin (PVL), Leukocidin ED (LukED), Gamma-Hemolysin and Clumping Factor A (ClfA), in a Rabbit Model of USA300 MRSA Prosthetic Joint Infection (PJI)," Open Forum Infectious Diseases 6(Suppl 2):S320-S321, Oxford University Press, United Kingdom (Oct. 3, 2019).
Yu, X-Q., et al., "Safety, Tolerability, and Pharmacokinetics of MEDI4893, an Investigational, Extended-Half-Life, Anti-Staphylococcus aureus Alpha-Toxin Human Monoclonal Antibody, in Healthy Adults," Antimicrob Agents Chemother 61(1):e01020-16, 9 pages, American Society for Microbiology, United States (Jan. 2017).
Vajdos, F.F., et al., "Comprehensive functional maps of the antigen-binding site of an anti-ErbB2 antibody obtained with shotgun scanning mutagenesis," J. Mol Biol 320(2):415-428, Elsevier, Netherlands (2002).
Brown, M., et al., "Tolerance of single, but not multiple, amino acid replacements in antibody VH CDR 2: a means of minimizing B cell wastage from somatic hypermutation?," The Journal of Immunology 156(9):3285-3291, American Association of Immunologists, United States (1996).
Office Action dated Nov. 3, 2020, in U.S. Appl. No. 16/596,445, inventor Tkaczyk, C., et al., filed Oct. 8, 2019, 7 pages.
Office Action dated Apr. 14, 2021, in U.S. Appl. No. 16/596,388, inventor Tkaczyk, C., et al., filed Oct. 8, 2019, 19 pages.
Office Action dated Oct. 2, 2020, in U.S. Appl. No. 16/596,388, inventor Tkaczyk, C., et al., filed Oct. 8, 2019, 17 pages.
International Search Report and Written opinion for International Application No. PCT/US2019/055143, European Patent Office, Netherlands dated Sep. 23, 2020, 22 pages.
Gershoni, J., et al., "Epitope mapping—The first step in developing epitope-based vaccines," BioDrugs 21(3):145-156, ADIS International LTD, New Zealand (2007).
Ortines, R., et al., "Efficacy of a Multimechanistic Monoclonal Antibody Combination against Staphylococcus aureus Surgical Site Infections in Mice," Antimicrobial Agents and Chemotherapy 63(8):e00346-19, 6 pages, American Society for Microbiology, United States (May 2019).

Figure 3

```
HlgB   GEGKITPVSVKKVDDKVTLYKTTATADSDKEKISQILTFNFIKDKSYDKDTLVLKATGNI   60
LukF   GAQHITPVSEKKVDDKITLYKTTATSDSDKLKISQILTFNFIKDKSYDKDTLILKAAGNI   60
LukD   GAQHITPVSEKKVDDKITLYKTTATSDNDKLNISQILTFNFIKDKSYDKDTLVLKAAGNI   60
       * :****.:****.**.*:**********:.**:*** ***.:*************.*.******

HlgB   NSGFVKPNPNDYDFSKLYWGAKYNVSISSQSNDSVNVVDYAPKNQNEEFQVQNTLGYTFG   120
LukF   YSGYTKPNPKDTISSQFYWGSKYNISINSDSNDSVNVVDYAPKNQNEEFQVQQTVGYSYG   120
LukD   NSGYKKPNPKDYNYSQFYWGGKYNVSVSSESNDAVNVVDYAPKNQNEEFQVQQTLGYSYG   120
       ***: :***:*   *: ***.***:*:.*:***:************:***:*.***. *

HlgB   GDISISNGLSGGLNGNTAFSETINYKQESYRTTLSRNTNYKNVGWGVEAHKIMNNGWGPY   180
LukF   GDINISNGLSGGGNGSKSFSETINYKQESYRTSLDKRTNFKKIGWDVEAHKIMNNGWGPY   180
LukD   GDINISNGLSGGLNGSKSFSETINYKQESYRTTIDRKTNHKSIGWGVEAHKIMNNGWGPY   180
       ***.********  **..: ************:: .:**:*  :**:************

HlgB   GRDSFHPTYGNELFLAGRQSSAYAGQNFIAQHQMPLLSRSNFNPEFLSVLSHRQDGAKKS   240
LukF   GRDSYHSTYGNEMFLGSRQSNLNAGQNFLEYHKMPVLSRGNFNPEFIGVLSRKQNAAKKS   240
LukD   GRDSYDPTYGNELFLGGRQSSNAGQNFLPTHQMPLLARGNFNPEFISVLSHKQNDTKKS   240
       ****:  *****:**..***.  ****: ::::**:*:.:*****: ***::*:.:***

HlgB   KITVTVYQREMDLYQIRWNGFYWAGANYKNFKTRTFKSTYEIDWENHKVKLLDTKETENNK   300
LukF   KITVTVYQREMDRYTNFWNQLHWIGNNYKDENRATHTSIYEVDWENHTVKLIDTQSKEKNP   300
LukD   KIKVTVYQREMDRYTNQWNRLHWGNNYKNQNTVTFTSTYEVDWQNHTVKLIGTDSKETNP   300
       **.********* *. :**. ** ****:::.. .:.: ***:**:**.***: *:.:*:*

HlgB   -- 300
LukF   MS 302
LukD   GV 302
```

ANTIBODIES DIRECTED AGAINST *STAPHYLOCOCCUS AUREUS* LEUKOTOXINS

CROSS REFERENCE TO RELATED APPLICATIONS

This application is a divisional of U.S. application Ser. No. 16/596,445, filed Oct. 8, 2019, which claims the priority benefit of U.S. Provisional Application No. 62/743,501, filed Oct. 9, 2018, each of which is hereby incorporated by reference herein in their entirety.

SEQUENCE LISTING

The content of the electronically submitted sequence listing (Name: 2943_1030003_Seqlisting_ST25.txt; Size: 49,784 bytes; and Date of Creation: Jun. 1, 2021) is hereby incorporated by reference.

BACKGROUND

Infections caused by antimicrobial resistant (AMR) bacterial pathogens are an increasing threat to public health. The ongoing AMR epidemic has been fueled, in part, by empiric broad spectrum antibiotic therapy. This has led to the exploration of pathogen-specific methods, including monoclonal antibodies (mAbs), to prevent or treat serious bacterial infections. Some monoclonal antibodies are currently in development for the prevention or treatment of antibiotic resistant bacterial infections (see, e.g., DiGiandomenico, A., and B. R. Sellman, *Curr. Opin. Microbiol.*, 27: 78-85 (2015)). Such passive immunization strategies provide an immediate and potent immunoglobulin response against the target pathogen.

*Staphylococcus aureus* is a bacterial pathogen that causes a wide array of diseases including skin and soft tissue infections, endocarditis, osteomyelitis, pneumonia, and bacteremia (Lowy, F. D., *N. Engl. J Med.*, 339(8): 520-32 (1998)). Preclinical studies indicate monoclonal antibody-based approaches hold promise for prophylaxis and adjunctive therapy against *S. aureus* infections (see, e.g., Hazenbos et al., *PLoS Pathog.*, 9(10):e1003653. doi: 10.1371/journal.ppat.10036532013 (2013); Rouha, H., *MAbs*, 7(1): 243-254 (2015); Foletti et al., *J. Mol. Biol.*, 425(10): 1641-1654 (2013); Karauzum et al., *J Biol Chem.*, 287(30): 25203-15 (2012); and Hua et al., *Antimicrob Agents Chemother.*, 58(2): 1108-17 (2014)). However, there remains a need for antibodies useful for treating *Staphylococcus aureus* infections, particularly infections that are resistant to currently-available antibiotics. The present disclosure provides such antibodies.

BRIEF SUMMARY OF THE INVENTION

Provided herein are antibodies and antigen-binding fragments thereof that bind to *Staphylococcus aureus* (*S. aureus*) leukotoxin.

In certain instances, an antibody or antigen-binding fragment thereof that specifically binds to at least one *S. aureus* leukotoxin comprises a variable heavy chain (VH) complementarity determining region (CDR) 1, a VH CDR2, a VH CDR3, a variable light chain (VL) CDR1, a VL CDR2, and a VL CDR3, wherein the VH CDR1, VH CDR2, VH CDR3, VL CDR1, VL CDR2, and VL CDR3 comprise sequences selected from the group consisting of: (a) SEQ ID NOs:1, 2, 3, 12, 5, and 6, respectively; (b) SEQ ID NOs:1-6, respectively; (c) SEQ ID NOs:1, 2, 17, 4, 5, and 6, respectively; (d) SEQ ID NOs: 1, 2, 17, 12, 5, and 6, respectively; and (e) SEQ ID NOs: 1, 20, 3, 4, 5, and 6, respectively.

In certain instances, an antibody or antigen-binding fragment thereof that specifically binds to at least one *S. aureus* leukotoxin comprises the VH CDR1, VH CDR2, VH CDR3, VL CDR1, VL CDR2, and VL CDR3 of SAN481-SYT-YTE. In certain instances, the CDRs are the Kabat-defined CDRs, the Chothia-defined CDRs, or the AbM-defined CDRs.

In certain instances, the antibody or antigen-binding fragment thereof comprises a VH and a VL, wherein the VH comprises the amino acid sequence of SEQ ID NO:7, 15, 18, 21, or 23. In certain instances, the antibody or antigen-binding fragment thereof comprises a VH and a VL, wherein the VL comprises the amino acid sequence of SEQ ID NO:8 or 13. In certain instances, the antibody or antigen-binding fragment thereof comprises a VH and a VL, wherein the VH and VL comprise sequences selected from the group consisting of: (a) SEQ ID NOs:15 and 13, respectively; (b) SEQ ID NOs:7 and 8, respectively; (c) SEQ ID NOs:7 and 13, respectively; (d) SEQ ID NOs:15 and 8, respectively; (e) SEQ ID NOs:18 and 8, respectively; (f) SEQ ID NOs:18 and 13, respectively; (g) SEQ ID NOs:21 and 8, respectively; and (h) SEQ ID NOs:23 and 13, respectively. In certain instances, the antibody or antigen-binding fragment thereof comprises a VH comprising the sequence of SEQ ID NO:15 and a VL comprising the sequence of SEQ ID NO:13. In certain instances, the antibody or antigen-binding fragment comprises a heavy chain comprising the sequence of SEQ ID NO:16, 9, 11, 22, or 24. In certain instances, the antibody or antigen-binding fragment comprises a light chain comprising the sequence of SEQ ID NO:14 or 10. In certain instances, the antibody comprises a heavy chain and a light chain, wherein the heavy and chains comprise sequences selected from the group consisting of: (a) SEQ ID NOs: 16 and 14, respectively; (b) SEQ ID NOs:9 and 10, respectively; (c) SEQ ID NOs:11 and 10, respectively; (d) SEQ ID NOs:11 and 14, respectively; (e) SEQ ID NOs:16 and 10, respectively; (f) SEQ ID NOs:19 and 10, respectively; (g) SEQ ID NOs:19 and 14, respectively; (h) SEQ ID NOs:22 and 10, respectively; and (i) SEQ ID NOs:24 and 14, respectively. In certain instances, the antibody comprises a heavy comprising the sequence of SEQ ID NO:16 and a light chain comprising the sequence of SEQ ID NO:14.

In certain instances, an antibody or antigen-binding fragment thereof provided herein binds to the same *S. aureus* leukotoxin epitope as an antibody comprising a VH comprising the amino acid sequence of SEQ ID NO:15 and a VL comprising the amino acid sequence of SEQ ID NO:13.

In certain instances, an antibody or antigen-binding fragment thereof provided herein competitively inhibits binding of an antibody comprising a VH comprising the amino acid sequence of SEQ ID NO:15 and a VL comprising the amino acid sequence of SEQ ID NO:13 to a *S. aureus* leukotoxin In certain instances, the antibody or antigen-binding fragment binds to LukF, LukD, or HlgB and/or the antibody or antigen-binding fragment neutralizes LukF, LukD, or HlgB. In certain instances, the antibody or antigen-binding fragment (a) binds to LukF, LukD, and HlgB and/or (b) neutralizes LukF, LukD, and HlgB.

In certain instances, the antibody or antigen-binding fragment further comprises a heavy chain constant region. In certain instances, the heavy chain constant region is selected from the group consisting of human immunoglobulin $IgG_1$, $IgG_2$, $IgG_3$, $IgG_4$, $IgA_1$, and $IgA_2$ heavy chain constant regions. In certain instances, the heavy chain constant region is a human $IgG_1$ constant region.

In certain instances, the antibody or antigen-binding fragment further comprises a light chain constant region. In certain instances, the light chain constant region is selected from the group consisting of human immunoglobulin IgGκ and IgGλ light chain constant regions. In certain instances, the light chain constant region is a human IgGκ light chain constant region.

In certain instances, the antibody or antigen-binding fragment thereof is an IgG antibody or antigen-binding fragment thereof.

In certain instances, the antibody or antigen-binding fragment comprises an Fc region that has been engineered to improve half-life. In certain instances, the antibody or antigen-binding fragment thereof comprises an Fc region with a YTE mutation.

In certain instances, the antibody or antigen-binding fragment is a monoclonal antibody or antigen-binding fragment.

In certain instances, the antibody or antigen-binding fragment is a full-length antibody. In certain instances, the antibody or antigen-binding fragment is an antigen-binding fragment. In certain instances, the antigen-binding fragment comprises a Fab, Fab', F(ab')2, single chain Fv (scFv), disulfide linked Fv, intrabody, IgGΔCH2, minibody, F(ab')$_3$, tetrabody, triabody, diabody, DVD-Ig, Fcab, mAb$^2$, (scFv)$_2$, or scFv-Fc.

In certain instances, the antibody or antigen-binding fragment thereof has an affinity of less than 75 pM for *S. aureus* LukF, LukD, and HlgB. In certain instances, the antibody or antigen-binding fragment thereof has similar binding affinities for LukF, LukD, and HlgB.

In certain instances, the antibody or antigen-binding fragment thereof further comprising a detectable label Provided herein are also compositions comprising an antibody or antigen-binding fragment thereof provided herein and, optionally, a pharmaceutically-acceptable carrier.

Provided herein are also methods of using an antibody provided herein. In certain instances, a method of treating or preventing a *Staphylococcus aureus* (*S. aureus*) infection in a subject comprises administering to the subject an antibody or antigen-binding fragment provided herein or a composition provided herein. In certain instances, the *S. aureus* infection is sepsis. In certain instances, the *S. aureus* infection is bacteremia. In certain instances, the *S. aureus* infection is pneumonia. In certain instances, the *S. aureus* infection is ICU pneumonia. In certain instances, the *S. aureus* infection is a skin or soft tissue infection (SSTI). In certain instances, the *S. aureus* infection is a diabetic infection of the lower limbs. In certain instances, the *S. aureus* infection is a diabetic foot ulcer (DFU). In certain instances, the DFU is uninfected. In certain instances, the DFU is infected. In certain instances, the DFU is a grade 1, 2 or 3 DFU. In certain instances, the *S. aureus* infection is a bone or joint infection. In certain instances, the *S. aureus* infection is a joint infection, a device infection, a wound infection, a surgical site infection, or osteomyelitis.

In certain instances, the subject is a surgical subject.

In certain instances, the *S. aureus* infection comprises antibiotic-resistant *S. aureus*.

In certain instances, the subject has diabetes.

In certain instances, the subject is human.

In certain instances, the treating or preventing an *S. aureus* infection comprises toxin neutralization, inhibiting cell lysis, inhibiting multi-organ dysfunction, inhibiting *S. aureus*-associated sepsis, or any combination of the foregoing.

Provided herein are also polynucleotides. In certain instances, an isolated polynucleotide comprises a nucleic acid molecule encoding the VH or heavy chain of an antibody or antigen-binding fragment thereof provided herein. In certain instances, an isolated polynucleotide comprises a nucleic acid molecule encoding the VL or light chain of an antibody or antigen-binding fragment thereof provided herein.

Also provided herein are vectors. In certain instances, a polynucleotide provided herein.

Also provided herein are host cells. In certain instances, a host cell comprises a polynucleotide provided herein, a vector provided herein, or a first vector a polynucleotide provided herein and a second vector comprising a polynucleotide provided herein. In certain instances, the host cell is selected from the group consisting of CHO, NS0, PER-C6, HEK-293, and HeLa cells. In certain instances, the host cell is isolated.

Also provided herein are methods of producing antibodies or antigen-binding fragments. In certain instances, a method of producing an antibody or antigen-binding fragment thereof comprises culturing a host cell provided herein so that the antibody or antigen-binding fragment thereof is produced.

Also provided herein are methods for detecting detecting *S. aureus* or *S. aureus* leukotoxin. In certain instances, a method for detecting *S. aureus* or *S. aureus* leukotoxin in a sample comprises contacting said sample with an antibody or antigen-binding fragment thereof provided herein.

BRIEF DESCRIPTION OF THE SEVERAL VIEWS OF THE DRAWING(S)

FIG. 1 provides graphs showing the in vitro activities of multiple SAN481 variants as compared to SAN481. QD1=SAN481-YTE; QD2=SAN481VL26S32Y-YTE; QD3=SAN481VH28T-YTE; QD4=SAN481-VH28T100E-YTE; QD5=SAN481-SY-T-YTE; QD6=SAN481-SY-TF-YTE; QD11=SAN481-EG-YTE; and QD12=SAN481-SY-QFS-YTE. (See Example 2.)

Figure 2:
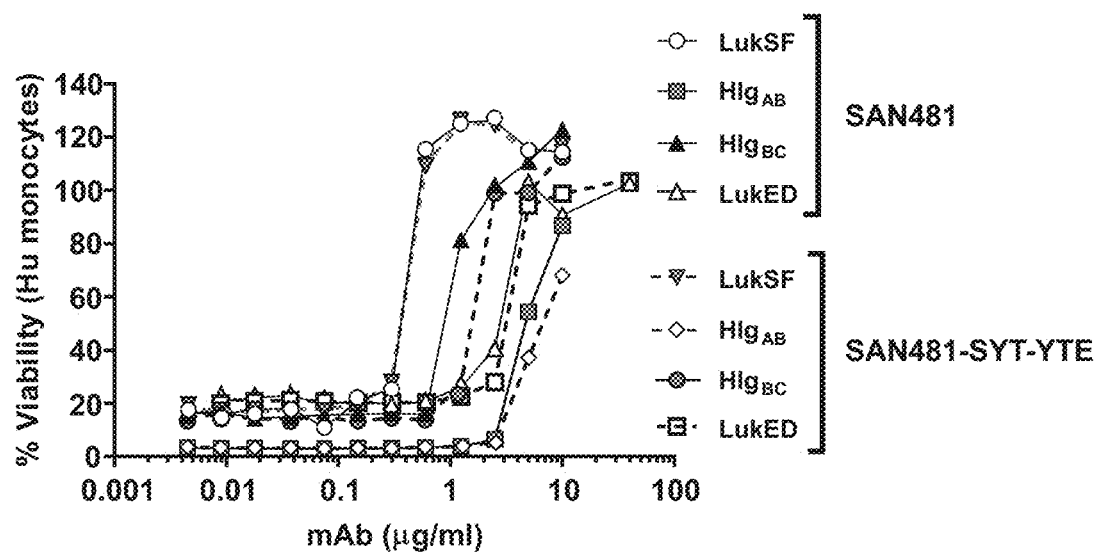

FIG. 2 provides a graph demonstrating that SAN481-SYT-YTE has similar in vitro leukotoxin neutralization activity as SAN481. (See Example 3.)

FIG. 3 provides a sequence alignment of HlgB (SEQ ID NO:27), LukF (SEQ ID NO:25), and LukD (SEQ ID NO:26).

DETAILED DESCRIPTION OF THE INVENTION

The present disclosure provides antibodies and antigen-binding fragments thereof (e.g., monoclonal antibodies and antigen-binding fragments thereof) that bind to *Staphylococcus aureus* (*S. aureus*) leukotoxins. The present disclosure also provides methods of using such antibodies and antigen-binding fragments, for example, in detecting *Staphylococcus aureus* (*S. aureus*) leukotoxins and in the treatment or prevention of *S. aureus* infections.

I. Definitions

As used herein, the term "leukotoxin" refers to bacterial leukotoxin polypeptides including, but not limited to, native leukotoxin polypeptides and isoforms of leukotoxin polypeptides. "Leukotoxin" encompasses a full-length, unprocessed leukotoxin polypeptides as well as forms of leukotoxin polypeptides that result from processing within the cell. Leukotoxins include LukSF, leukotoxin ED (LukED), HlgAB, HlgCB), and leukotoxin AB (LukAB, also known as LukGH). As used herein, the term "S. aureus LukF" refers to a polypeptide comprising the amino acid sequence of SEQ ID NO:25. As used herein, the term "S. aureus LukD" refers to a polypeptide comprising the amino acid sequence of SEQ ID NO:26. As used herein, the term "S. aureus HlgB" refers to a polypeptide comprising the amino acid sequence of SEQ ID NO:27. (See FIG. 3.) A "leukotoxin polynucleotide," "leukotoxin nucleotide," or "leukotoxin nucleic acid" refer to a polynucleotide encoding a leukotoxin.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, chimeric antibodies, humanized antibodies, human antibodies, fusion proteins comprising an antibody, and any other modified immunoglobulin molecule so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The term "monoclonal antibodies," as used herein, refers to antibodies that are produced by a single clone of B-cells and bind to the same epitope. In contrast, the term "polyclonal antibodies" refers to a population of antibodies that are produced by different B-cells and bind to different epitopes of the same antigen.

The term "antibody fragment" refers to a portion of an intact antibody. An "antigen-binding fragment," "antigen-binding domain," or "antigen-binding region," refers to a portion of an intact antibody that binds to an antigen. An antigen-binding fragment can contain the antigenic determining regions of an intact antibody (e.g., the complementarity determining regions (CDR)). Examples of antigen-binding fragments of antibodies include, but are not limited to Fab, Fab', F(ab')2, and Fv fragments, linear antibodies, and single chain antibodies. An antigen-binding fragment of an antibody can be derived from any animal species, such as rodents (e.g., mouse, rat, or hamster) and humans or can be artificially produced.

A whole antibody typically consists of four polypeptides: two identical copies of a heavy (H) chain polypeptide and two identical copies of a light (L) chain polypeptide. Each of the heavy chains contains one N-terminal variable (VH) region and three C-terminal constant (CH1, CH2 and CH3) regions, and each light chain contains one N-terminal variable (VL) region and one C-terminal constant (CL) region. The variable regions of each pair of light and heavy chains form the antigen binding site of an antibody. The VH and VL regions have the same general structure, with each region comprising four framework regions, whose sequences are relatively conserved. The term "framework region," as used herein, refers to the relatively conserved amino acid sequences within the variable region which are located between the hypervariable or complementarity determining regions (CDRs). There are four framework regions in each variable domain, which are designated FR1, FR2, FR3, and FR4. The framework regions form the β sheets that provide the structural framework of the variable region (see, e.g., C. A. Janeway et al. (eds.), Immunobiology, 5th Ed., Garland Publishing, New York, N.Y. (2001)). The three CDRs, known as CDR1, CDR2, and CDR3, form the "hypervariable region" of an antibody, which is responsible for antigen binding.

The terms "VL" and "VL domain" are used interchangeably to refer to the light chain variable region of an antibody.

The terms "VH" and "VH domain" are used interchangeably to refer to the heavy chain variable region of an antibody.

The term "Kabat numbering" and like terms are recognized in the art and refer to a system of numbering amino acid residues in the heavy and light chain variable regions of an antibody or an antigen-binding fragment thereof. In certain aspects, CDRs can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
|------|-------|-----|---------|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32..34 (Kabat Numbering) |
| H1 | H31-H35 | H26-H35 | H26-H32 (Chothia Numbering) |
| H2 | H50-H65 | H50-H58 | H52-H56 |
| H3 | H95-H102 | H95-H102 | H95-H102 |

As used herein, the term "constant region" or "constant domain" are interchangeable and have its meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

As used herein, the term "heavy chain" when used in reference to an antibody can refer to any distinct type, e.g., alpha (α), delta (δ), epsilon (ε), gamma (γ), and mu (μ), based on the amino acid sequence of the constant domain, which give rise to IgA, IgD, IgE, IgG, and IgM classes of antibodies, respectively, including subclasses of IgG, e.g., $IgG_1$, $IgG_2$, $IgG_3$, and $IgG_4$. Heavy chain amino acid sequences are well known in the art. In specific embodiments, the heavy chain is a human heavy chain.

As used herein, the term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

A "chimeric" antibody refers to an antibody or fragment thereof comprising both human and non-human regions. A "humanized" antibody is a antibody comprising a human antibody scaffold and at least one CDR obtained or derived from a non-human antibody. Non-human antibodies include antibodies isolated from any non-human animal, such as, for example, a rodent (e.g., a mouse or rat). A humanized antibody can comprise, one, two, or three CDRs obtained or derived from a non-human antibody. A fully human antibody does not contain any amino acid residues obtained or derived from a non-human animal. It will be appreciated that fully human and humanized antibodies carry a lower risk for inducing immune responses in humans than mouse or chimeric antibodies (see, e.g., Harding et al., *mAbs,* 2(3): 256-26 (2010)).

As used herein, an "epitope" is a term in the art and refers to a localized region of an antigen to which an antibody or antigen-binding fragment thereof can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody or antigen-binding fragment thereof binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization can be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody/antigen-binding fragment thereof: antigen crystals can be studied using well known X-ray diffraction techniques and can be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies can be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques.

An antibody that "binds to the same epitope" as a reference antibody refers to an antibody that binds to the same amino acid residues as the reference antibody. The ability of an antibody to bind to the same epitope as a reference antibody can determined by a hydrogen/deuterium exchange assay (see Coales et al. Rapid Commun. Mass Spectrom. 2009; 23: 639-647) or x-ray crystallography.

As used herein, the terms "immunospecifically binds," "immunospecifically recognizes," "specifically binds," and "specifically recognizes" are analogous terms in the context of antibodies or antigen-binding fragments thereof. These terms indicate that the antibody or antigen-binding fragment thereof binds to an epitope via its antigen-binding domain and that the binding entails some complementarity between the antigen binding domain and the epitope. Accordingly, for example, an antibody that "specifically binds" to a first *S. aureus* leukotoxin may also bind to other *S. aureus* leukotoxins, but the extent of binding to an un-related, non-leukotoxin protein is less than about 10% of the binding of the antibody to the first *S. aureus* leukotoxin as measured, e.g., by a radioimmunoassay (RIA), enzyme-linked immunosorbent assay (ELISA), BiaCore or an octet binding assay.

An antibody is said to "competitively inhibit" binding of a reference antibody to a given epitope if it preferentially binds to that epitope or an overlapping epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

The term "nucleic acid sequence" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides. Nucleic acids are typically linked via phosphate bonds to form nucleic acid sequences or polynucleotides, though many other linkages are known in the art (e.g., phosphorothioates, boranophosphates, and the like).

An *S. aureus* infection can occur, for example, as a skin or soft tissue infection (SSTI) or bacteremia. *S. aureus* bacteria can travel through the bloodstream and infect a site in the body, resulting in pneumonia, ICU pneumonia, a diabetic infection of the lower limbs, diabetic foot ulcer (DFU), a bone or joint infection, a device infection, a wound infection, a surgical site infection, or osteomyelitis.

"Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), *Methods in Molecular Biology, Vol. 7, Gene Transfer and Expression Protocols,* Humana Press (1991)); DEAE-dextran; electroporation; cationic liposome-mediated transfection; tungsten particle-facilitated microparticle bombardment (Johnston, *Nature,* 346: 776-777 (1990)); and strontium phosphate DNA co-precipitation (Brash et al, *Mol. Cell Biol.,* 7: 2031-2034 (1987)). Phage or viral vectors can be introduced into host cells, after growth of infectious particles in suitable packaging cells, many of which are commercially available.

As used herein, the terms "treatment," "treating," and the like, refer to obtaining a desired pharmacologic and/or physiologic effect. In one embodiment, the effect is therapeutic, i.e., the effect partially or completely cures a disease and/or adverse symptom attributable to the disease.

A "therapeutically effective amount" refers to an amount effective, at dosages and for periods of time necessary, to achieve a desired therapeutic result (e.g., treatment of *S. aureus* infection). The therapeutically effective amount may vary according to factors such as the disease state, age, sex, and weight of the individual, and the ability of the antibody or antigen-binding fragment to elicit a desired response in the individual.

A "prophylactically effective amount" refers to an amount effective, at dosages and for periods of time necessary, to achieve a desired prophylactic result (e.g., prevention of *S. aureus* infection or disease onset).

The terms "administer", "administering", "administration", and the like, as used herein, refer to methods that may be used to enable delivery of a drug, e.g., a leukotxin-binding antibody or antigen-binding fragment thereof to the desired site of biological action (e.g., intravenous administration). Administration techniques that can be employed with the agents and methods described herein are found in e.g., Goodman and Gilman, *The Pharmacological Basis of Therapeutics,* current edition, Pergamon; and Remington's, *Pharmaceutical Sciences,* current edition, Mack Publishing Co., Easton, Pa.

As used in the present disclosure and claims, the singular forms "a," "an," and "the" include plural forms unless the context clearly dictates otherwise.

Unless specifically stated or obvious from context, as used herein, the term "or" is understood to be inclusive. The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. Anti-Leukotoxin Antibodies

Provided herein are antibodies and antigen-binding fragments thereof that bind to at least one *S. aureus* leukotoxin.

Leukotoxins are *S. aureus* virulence factor. Leukotoxins target a broad range of immune cells for destruction. Leukotoxins include Panton-Valentine leukocidin (LukSF-PV also known as LukSF), leukotoxin ED (LukED), gamma hemolysin (which exists as two toxins: HlgAB and HlgCB), and leukotoxin AB (LukAB, also known as LukGH). In certain instances, an antibody or antigen-binding fragment thereof that binds to at least one leukotoxin binds to LukF, LukD, and/or HlgB. In certain instances, an antibody or antigen-binding fragment thereof that binds to at least one leukotoxin binds to LukF, LukD, and HlgB.

In one instance, an antibody or antigen-binding fragment (e.g., monoclonal antibody or fragment) that specifically binds to at least one *S. aureus* leukotoxin comprises, consists essentially of, or consists of (i) a heavy chain polypeptide comprising a CDR1 amino acid sequence of SEQ ID NO:1, a CDR2 amino acid sequence of SEQ ID NO:2, and a CDR3 amino acid sequence of SEQ ID NO:3, and (ii) a light chain polypeptide comprising a CDR1 amino acid sequence of SEQ ID NO:12, a CDR2 amino acid sequence of SEQ ID NO:5, and a CDR3 amino acid sequence of SEQ ID NO:6. In another instance, the heavy chain polypeptide of an antibody or antigen-binding fragment (e.g., monoclonal antibody or fragment) that specifically binds to at least one *S. aureus* leukotoxin comprises, consists essentially of, or consists of a variable region amino acid sequence of SEQ ID NO:15. In another instance, the light chain polypeptide of an antibody or antigen-binding fragment (e.g., monoclonal antibody or fragment) that specifically binds to at least one *S. aureus* leukotoxin comprises, consists essentially of, or consists of a variable region amino acid sequence of SEQ ID NO:13. In another instance, an antibody or antigen-binding fragment (e.g., monoclonal antibody or fragment) that specifically binds to at least one *S. aureus* leukotoxin comprises, consists essentially of, or consists of a variable heavy chain comprising, consisting essentially of, or consisting of the amino acid sequence of SEQ ID NO:15 and a variable light chain comprising, consisting essentially of, or consisting of the amino acid sequence of SEQ ID NO:13. In another instance, an antibody or antigen-binding fragment (e.g., monoclonal antibody or fragment) that specifically binds to at least one *S. aureus* leukotoxin comprises, consists essentially of, or consists of a variable heavy chain comprising, consisting essentially of, or consisting of the amino acid sequence of SEQ ID NO:16 and/or a variable light chain comprising, consisting essentially of, or consisting of the amino acid sequence of SEQ ID NO:14.

Sequences of exemplary anti-leukotoxin antibodies are provided below. In certain instances, an antibody or antigen-binding fragment thereof described herein binds to at least one leukotoxin and comprises six CDRs (i.e., a VH CDR1, a VH CDR2, a VH CDR3, a VL CDR1, a VL CDR2, and VL CDR3) from Tables 1 and 2 below.

The SAN481-SYT-YTE antibody comprises the VH CDRs of SEQ ID NOs:1-3 and the VL CDRs of SEQ ID NOs:12, 5, and 6.

TABLE 1

VH CDR Amino Acid Sequences

| Antibody Name | VH CDR1 (SEQ ID NO:) | VH CDR2 (SEQ ID NO:) | VH CDR3 (SEQ ID NO:) |
|---|---|---|---|
| SAN481 | TYAMH (SEQ ID NO: 1) | VTSFDGSNEYY IDSVKG (SEQ ID NO: 2) | DEYTGGWYSVGY (SEQ ID NO: 3) |
| SAN481-TF | TYAMH (SEQ ID NO: 1) | VTSFDGSNEYY IDSVKG (SEQ ID NO: 2) | DEYTGGFYSVGY (SEQ ID NO: 17) |
| SAN481-EG | TYAMH (SEQ ID) NO: 1 | VTSFEGSNEYY IDSVKG (SEQ ID NO: 20) | DEYTGGWYSVGY (SEQ ID NO: 3) |

TABLE 2

VL CDR Amino Acid Sequences

| Antibody | VL CDR1 (SEQ ID NO:) | VL CDR2 (SEQ ID NO:) | VL CDR3 (SEQ ID NO:) |
|---|---|---|---|
| SAN481 | SGNSYNIGSNSVY (SEQ ID NO: 4) | RSIQRPS (SEQ ID NO: 5) | AAWDDSLRAWV (SEQ ID NO: 6) |
| SAN481-SY | SGSSYNIGSNYVY (SEQ ID NO: 12) | RSIQRPS (SEQ ID NO: 5) | AAWDDSLRAWV (SEQ ID NO: 6) |

In certain instances, an antibody or antigen-binding fragment thereof described herein binds to at least one leukotoxin and comprises the VH of an antibody listed in the following table, e.g., in combination with a VL.

TABLE 3

Variable Heavy Chain (VH) Amino Acid Sequence

| Antibody | VH Amino Acid Sequence (SEQ ID NO) |
|---|---|
| SAN481 | QLQLVESGGGAVQPGRSLKLSCAASGFNFSTYAMHW VRQAPGRGLEWVAVTSFDGSNEYYIDSVKGRFTISR DNTKNTLYLQMTGLRVEDTALYFCARDEYTGGWYSV GYWGQGTLVTVSS (SEQ ID NO: 7) |
| SAN481-T | QLQLVESGGGAVQPGRSLKLSCAASGFTFSTYAMHW VRQAPGRGLEWVAVTSFDGSNEYYIDSVKGRFTISR DNTKNTLYLQMTGLRVEDTALYFCARDEYTGGWYSV GYWGQGTLVTVSS (SEQ ID NO: 15) |
| SAN481-TF | QLQLVESGGGAVQPGRSLKLSCAASGFTFSTYAMHW VRQAPGRGLEWVAVTSFDGSNEYYIDSVKGRFTISR DNTKNTLYLQMTGLRVEDTALYFCARDEYTGGFYSV GYWGQGTLVTVSS (SEQ ID NO: 18) |

TABLE 3-continued

Variable Heavy Chain (VH) Amino Acid Sequence

| Antibody | VH Amino Acid Sequence (SEQ ID NO) |
|---|---|
| SAN481-EG | QLQLVESGGGAVQPGRSLKLSCAASGFNFSTYAMHW VRQAPGRGLEWVAVTSFEGSNEYYIDSVKGRFTISR DNTKNTLYLQMTGLRVEDTALYFCARDEYTGGWYSV GYWGQGTLVTVSS (SEQ ID NO: 21) |
| SAN481-QFS | QLQLVESGGGAVQPGRSLKLSCAASGFQFSTYAMHW VRQAPGRGLEWVAVTSFDGSNEYYIDSVKGRFTISR DNTKNTLYLQMTGLRVEDTALYFCARDEYTGGWYSV GYWGQGTLVTVSS (SEQ ID NO: 23) |

In certain instances, an antibody or antigen-binding fragment thereof described herein binds to at least one leukotoxin and comprises the VL of an antibody listed in the following table, e.g., in combination with a VH, optionally a VH listed in the preceding table.

TABLE 4

Variable Light Chain (VL) Amino Acid Sequence

| Antibody | VL Amino Acid Sequence (SEQ ID NO) |
|---|---|
| SAN481 | QSVLTQPPSASGTPGQRVTISCSGNSYNIGSNSV YWYQQFPGTAPKLLISRSIQRPSGVPDRFSGSKS VTSASLAISGLRSEDEADYYCAAWDDSLRAWVFG GGTKLTVL (SEQ ID NO: 8) |
| SAN481-SY | QSVLTQPPSASGTPGQRVTISCSGSSYNIGSNYV YWYQQFPGTAPKLLISRSIQRPSGVPDRFSGSKS VTSASLAISGLRSEDEADYYCAAWDDSLRAWVFG GGTKLTVL (SEQ ID NO: 13) |

In certain instances, an antibody or antigen-binding fragment thereof described herein binds at least one leukotoxin and comprises the heavy chain of an antibody listed in the following table, e.g., in combination with a light chain.

TABLE 5

Full-length heavy chain amino acid sequences

| Antibody | Full-Length Heavy Chain Amino Acid Sequence (SEQ ID NO) |
|---|---|
| SAN481 | QLQLVESGGGAVQPGRSLKLSCAASGFNFSTYAMHWVRQAPGRGLEW VAVTSFDGSNEYYIDSVKGRFTISRDNTKNTLYLQMTGLRVEDTALYFC ARDEYTGGWYSVGYWGQGTLVTVSSASTKGPSVFPLAPSSKSTSGGTA ALGCLVKDYFPEPVTVSWNSGALTSGVHTFPAVLQSSGLYSLSSVVTVP SSSLGTQTYICNVNHKPSNTKVDKRVEPKSCDKTHTCPPCPAPELLGGP SVFLFPPKPKDTLMISRTPEVTCVVVDVSHEDPEVKFNWYVDGVEVHN AKTKPREEQYNSTYRVVSVLTVLHQDWLNGKEYKCKVSNKALPAPIE KTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHE ALHNHYTQKSLSLSPGK (SEQ ID NO: 9) |
| SAN481-YTE | QLQLVESGGGAVQPGRSLKLSCAASGFNFSTYAMHWVRQAPGRGLEW VAVTSFDGSNEYYIDSVKGRFTISRDNTKNTLYLQMTGLRVEDTALYFC ARDEYTGGWYSVGYWGQGTLVTVSSASTKGPSVFPLAPSSKSTSGGTA ALGCLVKDYFPEPVTVSWNSGALTSGVHTFPAVLQSSGLYSLSSVVTVP SSSLGTQTYICNVNHKPSNTKVDKRVEPKSCDKTHTCPPCPAPELLGGP SVFLFPPKPKDTLYITREPEVTCVVVDVSHEDPEVKFNWYVDGVEVHN AKTKPREEQYNSTYRVVSVLTVLHQDWLNGKEYKCKVSNKALPAPIE KTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHE ALHNHYTQKSLSLSPGK (SEQ ID NO: 11) |
| SAN481-T-YTE | QLQLVESGGGAVQPGRSLKLSCAASGFTFSTYAMHWVRQAPGRGLEW VAVTSFDGSNEYYIDSVKGRFTISRDNTKNTLYLQMTGLRVEDTALYFC ARDEYTGGWYSVGYWGQGTLVTVSSASTKGPSVFPLAPSSKSTSGGTA ALGCLVKDYFPEPVTVSWNSGALTSGVHTFPAVLQSSGLYSLSSVVTVP SSSLGTQTYICNVNHKPSNTKVDKRVEPKSCDKTHTCPPCPAPELLGGP SVFLFPPKPKDTLYITREPEVTCVVVDVSHEDPEVKFNWYVDGVEVHN |

TABLE 5-continued

Full-length heavy chain amino acid sequences

| Antibody | Full-Length Heavy Chain Amino Acid Sequence (SEQ ID NO) |
|---|---|
|  | AKTKPREEQYNSTYRVVSVLTVLHQDWLNGKEYKCKVSNKALPAPIE KTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHE ALHNHYTQKSLSLSPGK (SEQ ID NO: 16) |
| SAN481-TF-YTE | QLQLVESGGGAVQPGRSLKLSCAASGFTFSTYAMHWVRQAPGRGLEW VAVTSFDGSNEYYIDSVKGRFTISRDNTKNTLYLQMTGLRVEDTALYFC ARDEYTGGFYSVGYWGQGTLVTVSSASTKGPSVFPLAPS SKSTSGGTA ALGCLVKDYFPEPVTVSWNSGALTSGVHTFPAVLQSSGLYSLSSVVTVP SSSLGTQTYICNVNHKPSNTKVDKRVEPKSCDKTHTCPPCPAPELLGGP SVFLFPPKPKDTLYITREPEVTCVVVDVSHEDPEVKFNWYVDGVEVHN AKTKPREEQYNSTYRVVSVLTVLHQDWLNGKEYKCKVSNKALPAPIE KTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHE ALHNHYTQKSLSLSPGK (SEQ ID NO: 19) |
| SAN481-EG-YTE | QLQLVESGGGAVQPGRSLKLSCAASGFNFSTYAIVIRWVRQAPGRGLEW VAVTSFEGSNEYYIDSVKGRFTISRDNTKNTLYLQMTGLRVEDTALYFC ARDEYTGGWYSVGYWGQGTLVTVSSASTKGPSVFPLAPSSKSTSGGTA ALGCLVKDYFPEPVTVSWNSGALTSGVHTFPAVLQSSGLYSLSSVVTVP SSSLGTQTYICNVNHKPSNTKVDKRVEPKSCDKTHTCPPCPAPELLGGP SVFLFPPKPKDTLYITREPEVTCVVVDVSHEDPEVKFNWYVDGVEVHN AKTKPREEQYNSTYRVVSVLTVLHQDWLNGKEYKCKVSNKALPAPIE KTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHE ALHNHYTQKSLSLSPGK (SEQ ID NO: 22) |
| SAN481-QFS-YTE | QLQLVESGGGAVQPGRSLKLSCAASGFQFSTYAMHWVRQAPGRGLEW VAVTSFDGSNEYYIDSVKGRFTISRDNTKNTLYLQMTGLRVEDTALYFC ARDEYTGGWYSVGYWGQGTLVTVSSASTKGPSVFPLAPSSKSTSGGTA ALGCLVKDYFPEPVTVSWNSGALTSGVHTFPAVLQSSGLYSLSSVVTVP SSSLGTQTYICNVNHKPSNTKVDKRVEPKSCDKTHTCPPCPAPELLGGP SVFLFPPKPKDTLYITREPEVTCVVVDVSHEDPEVKFNWYVDGVEVHN AKTKPREEQYNSTYRVVSVLTVLHQDWLNGKEYKCKVSNKALPAPIE KTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHE ALHNHYTQKSLSLSPGK (SEQ ID NO: 24) |
| SAN481-T | QLQLVESGGGAVQPGRSLKLSCAASGFTFSTYAIVIRWVRQAPGRGLEW VAVTSFDGSNEYYIDSVKGRFTISRDNTKNTLYLQMTGLRVEDTALYFC ARDEYTGGWYSVGYWGQGTLVTVSSASTKGPSVFPLAPSSKSTSGGTA ALGCLVKDYFPEPVTVSWNSGALTSGVHTFPAVLQSSGLYSLSSVVTVP SSSLGTQTYICNVNHKPSNTKVDKRVEPKSCDKTHTCPPCPAPELLGGP SVFLFPPKPKDTLMISRTPEVTCVVVDVSHEDPEVKFNWYVDGVEVHN AKTKPREEQYNSTYRVVSVLTVLHQDWLNGKEYKCKVSNKALPAPIE KTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHE ALHNHYTQKSLSLSPGK (SEQ ID NO: 28) |

In certain instances, an antibody or antigen-binding fragment thereof described herein binds to at least one leukotoxin and comprises the light chain of an antibody listed in the following table, e.g., in combination with a heavy chain, optionally a heavy chain listed in the preceding table.

TABLE 6

Full-length light chain amino acid sequences

| Antibody | Full-Length Light Chain Amino Acid Sequence (SEQ ID NO) |
|---|---|
| SAN481 | QSVLTQPPSASGTPGQRVTISCSGSGNSYNIGSNSVYWYQQF PGTAPKLLISRSIQRPSGVPDRFSGSKSVTSASLAISGLR SEDEADYYCAAWDDSLRAWVFGGGTKLTVLGQPKAAPSVT LFPPSSEELQANKATLVCLISDFYPGAVTVAWKADSSPVK AGVETTTPSKQSNNKYAASSYLSLTPEQWKSHRSYS CQVTHEGSTVEKTVAPTECS (SEQ ID NO: 10) |
| SAN481-SY | QSVLTQPPSASGTPGQRVTISCSGSSYNIGSNYVYWYQQF PGTAPKLLISRSIQRPSGVPDRFSGSKSVTSASLAISGLR SEDEADYYCAAWDDSLRAWVFGGGTKLTVLGQPKAAPSVT LFPPSSEELQANKATLVCLISDFYPGAVTVAWKADSSPVK AGVETTTPSKQSNNKYAASSYLSLTPEQWKSHRSYS CQVTHEGSTVEKTVAPTECS (SEQ ID NO: 14) |

The sequences of antibodies used in the Examples below are summarized in Table 7.

TABLE 7

SEQ ID NOs of Antibody CDR, Variable Regions, and Heavy and Light Chains

| Antibody | H CDRs | L CDRs | VH | VL | H | L |
|---|---|---|---|---|---|---|
| SAN481 | 1-3 | 4-6 | 7 | 8 | 9 | 10 |
| SAN481-YTE | 1-3 | 4-6 | 7 | 8 | 11 | 10 |
| SAN481-SY-YTE | 1-3 | 12, 5, 6 | 7 | 13 | 11 | 14 |
| SAN481-T-YTE | 1-3 | 4-6 | 15 | 8 | 16 | 10 |
| SAN481-TF-YTE | 1, 2, 17 | 4-6 | 18 | 8 | 19 | 10 |
| SAN481-SYT-YTE | 1-3 | 12, 5, 6 | 15 | 13 | 16 | 14 |
| SAN481-SY-TF-YTE | 1, 2, 17 | 12, 5, 6 | 18 | 13 | 19 | 14 |
| SAN481-EG-YTE | 1, 20, 3 | 4-6 | 21 | 8 | 22 | 10 |
| SAN481-SY-QFS-YTE | 1-3 | 12, 5, 6 | 23 | 13 | 24 | 14 |
| SAN481-SYT* | 1-3 | 12, 5, 6 | 15 | 13 | 28 | 14 |

In certain aspects, the CDRs of an antibody or antigen-binding fragment thereof can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain aspects, provided herein antibodies and antigen-binding fragments thereof that comprise the Chothia VH and VL CDRs of the SAN481 or SAN481-SYT antibody. In certain embodiments, antibodies or antigen-binding fragments thereof comprise one or more CDRs, in which the Chothia and Kabat CDRs have the same amino acid sequence. In certain embodiments, provided herein are antibodies and antigen-binding fragments thereof comprise combinations of Kabat CDRs and Chothia CDRs.

In certain aspects, the CDRs of an antibody or antigen-binding fragment thereof can be determined according to the IMGT numbering system as described in Lefranc M-P, (1999) The Immunologist 7: 132-136 and Lefranc M-P et al., (1999) Nucleic Acids Res 27: 209-212. According to the IMGT numbering scheme, VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97. In a particular embodiment, provided herein are antibodies and antigen-binding fragments thereof that comprise the IMGT VH and VL CDRs of the SAN481 or SAN481-SYT-YTE antibody, for example, as described in Lefranc M-P (1999) supra and Lefranc M-P et al., (1999) supra).

In certain aspects, the CDRs of an antibody or antigen-binding fragment thereof can be determined according to MacCallum R M et al., (1996) J Mol Biol 262: 732-745. See also, e.g., Martin A. "Protein Sequence and Structure Analysis of Antibody Variable Domains," in *Antibody Engineering*, Kontermann and Dübel, eds., Chapter 31, pp. 422-439, Springer-Verlag, Berlin (2001). In a particular embodiment, provided herein are antibodies or antigen-binding fragments thereof that comprise the VH and VL CDRs of the SAN481 or SAN481-SYT-YTE antibody determined by the method in MacCallum R M et al.

In certain aspects, the CDRs of an antibody or antigen-binding fragment thereof can be determined according to the AbM numbering scheme, which refers AbM hypervariable regions which represent a compromise between the Kabat CDRs and Chothia structural loops, and are used by Oxford Molecular's AbM antibody modeling software (Oxford Molecular Group, Inc.). In a particular embodiment, provided herein are antibodies or antigen-binding fragments that comprise the VH and VL CDRs of the SAN481 or SAN481-SYT-YTE antibody as determined by the AbM numbering scheme.

In another aspect, the antibody or antigen-binding fragment thereof (e.g., monoclonal antibody or fragment) described herein can comprise a constant region (Fc) of any suitable class (e.g., IgG, IgA, IgD, IgM, and IgE) that has been modified in order to improve the half-life of the antibody or antigen-binding fragment (e.g., monoclonal antibody or fragment). For example, the antibody or antigen-binding fragment thereof (e.g., monoclonal antibody or fragment) described herein can comprise an Fc that comprises a mutation that extends half-life relative to the same antibody without the mutation.

Fc region engineering is widely used in the art to extend the half-life of therapeutic antibodies and protect from degradation in vivo. In some embodiments, the Fc region of an IgG antibody or antigen-binding fragment can be modified in order to increase the affinity of the IgG molecule for the Fc Receptor-neonate (FcRn), which mediates IgG catabolism and protects IgG molecules from degradation. Suitable Fc region amino acid substitutions or modifications are known in the art and include, for example, the triple substitution M252Y/S254T/T256E (referred to as "YTE") (see, e.g., U.S. Pat. No. 7,658,921; U.S. Patent Application Publication 2014/0302058; and Yu et al., *Antimicrob. Agents Chemother.*, 61(1): e01020-16 (2017)). In certain aspects, an antibody or antigen-binding binding fragment (e.g., monoclonal antibody or fragment) that binds to at least one *S. aureus* leukotoxin comprises an Fc region comprising the YTE mutation.

An antibody or antigen-binding fragment (e.g. monoclonal antibody or fragment) described herein can be, or can be obtained from, a human antibody, a humanized antibody, a non-human antibody, or a chimeric antibody. In one aspect, an antibody described herein, or antigen-binding fragment thereof, is a fully human antibody.

A human antibody, a non-human antibody, a chimeric antibody, or a humanized antibody can be obtained by any means, including via in vitro sources (e.g., a hybridoma or a cell line producing an antibody recombinantly) and in vivo sources (e.g., rodents, human tonsils). Methods for generating antibodies are known in the art and are described in, for example, Köhler and Milstein, *Eur. J. Immunol.*, 5: 511-519 (1976); Harlow and Lane (eds.), *Antibodies: A Laboratory Manual*, CSH Press (1988); and Janeway et al. (eds.), *Immunobiology, 5th Ed.*, Garland Publishing, New York, N.Y. (2001)). In certain embodiments, a human antibody or a chimeric antibody can be generated using a transgenic animal (e.g., a mouse) wherein one or more endogenous immunoglobulin genes are replaced with one or more human immunoglobulin genes. Examples of transgenic mice wherein endogenous antibody genes are effectively replaced with human antibody genes include, but are not limited to, the Medarex HUMAB-MOUSE™, the Kirin TC MOUSE™, and the Kyowa Kirin KM-MOUSE™ (see, e.g., Lonberg, *Nat. Biotechnol.*, 23(9): 1117-25 (2005), and Lonberg, *Handb. Exp. Pharmacol.*, 181: 69-97 (2008)). A humanized antibody can be generated using any suitable method known in the art (see, e.g., An, Z. (ed.), *Therapeutic Monoclonal Antibodies: From Bench to Clinic*, John Wiley & Sons, Inc., Hoboken, N.J. (2009)), including, e.g., grafting of non-human CDRs onto a human antibody scaffold (see, e.g., Kashmiri et al., *Methods*, 36(1): 25-34 (2005); and Hou et al., *J. Biochem.*, 144(1): 115-120 (2008)). In one embodiment, a humanized antibody can be produced using the methods described in, e.g., U.S. Patent Application Publication 2011/0287485 A1.

In certain aspects, an antibody or antigen-binding fragment provided herein has similar binding affinities for LukF, LukD, and HlgB.

III. Nucleic Acids, Vectors, and Host Cells

Also provided herein are one or more isolated nucleic acid sequences that encode the antibody or antigen-binding fragment thereof that binds to at least one leukotoxin (optionally wherein the antibody or antigen-binding fragment thereof is a monoclonal antibody or fragment).

The disclosure further provides one or more vectors comprising one or more nucleic acid sequences encoding an antibody or antigen-binding fragment thereof that binds to at least one leukotoxin (optionally wherein one or more of the antibodies or antigen-binding fragments thereof is a monoclonal antibody or fragment). The vector can be, for example, a plasmid, episome, cosmid, viral vector (e.g., retroviral or adenoviral), or phage. Suitable vectors and methods of vector preparation are well known in the art (see, e.g., Sambrook et al., *Molecular Cloning, a Laboratory Manual*, 3rd edition, Cold Spring Harbor Press, Cold Spring Harbor, N.Y. (2001), and Ausubel et al., *Current Protocols in Molecular Biology*, Greene Publishing Associates and John Wiley & Sons, New York, N.Y. (1994)).

In addition to the nucleic acid sequence encoding the antibody or antigen-binding fragment thereof that binds to at least one leukotoxin (optionally wherein the antibody or antigen-binding fragments thereof is a monoclonal antibody or fragment), the vector desirably comprises expression control sequences, such as promoters, enhancers, polyadenylation signals, transcription terminators, internal ribosome entry sites (IRES), and the like, that provide for the expression of the coding sequence in a host cell. Exemplary expression control sequences are known in the art and described in, for example, Goeddel, *Gene Expression Technology: Methods in Enzymology*, Vol. 185, Academic Press, San Diego, Calif. (1990).

The vector(s) comprising the nucleic acid(s) the antibody or antigen-binding fragment thereof that binds to at least one leukotoxin (optionally wherein one or more of the antibodies or antigen-binding fragments thereof is a monoclonal antibody or fragment) can be introduced into a host cell that is capable of expressing the polypeptides encoded thereby, including any suitable prokaryotic or eukaryotic cell. As such, the present disclosure provides an isolated cell comprising the vector. Host cells that may be used include those that can be easily and reliably grown, have reasonably fast growth rates, have well characterized expression systems, and can be transformed or transfected easily and efficiently. Examples of suitable prokaryotic cells include, but are not limited to, cells from the genera *Bacillus* (such as *Bacillus subtilis* and *Bacillus brevis*), *Escherichia* (such as *E. coli*), *Pseudomonas*, *Streptomyces*, *Salmonella*, and *Erwinia*. Particularly useful prokaryotic cells include the various strains of *Escherichia coli* (e.g., K12, HB101 (ATCC® No. 33694), DH5a, DH10, MC1061 (ATCC® No. 53338), and CC102). Suitable eukaryotic cells are known in the art and include, for example, yeast cells, insect cells, and mammalian cells. In one embodiment, the vector is expressed in mammalian cells. A number of suitable mammalian host cells are known in the art, and many are available from the American Type Culture Collection (ATCC®, Manassas, Va.). Examples of suitable mammalian cells include, but are not limited to, Chinese hamster ovary cells (CHO) (ATCC® No. CCL61), CHO DHFR-cells (Urlaub et al, *Proc. Natl. Acad. Sci. USA*, 97: 4216-4220 (1980)), human embryonic kidney (HEK) 293 or 293T cells (ATCC® No. CRL1573), and 3T3 cells (ATCC® No. CCL92). Other suitable mammalian cell lines are the monkey COS-1 (ATCC® No. CRL1650) and COS-7 cell lines (ATCC® No. CRL1651), as well as the CV-1 cell line (ATCC® No. CCL70). The mammalian cell desirably is a human cell. For example, the mammalian cell can be a human lymphoid or lymphoid derived cell line, such as a cell line of pre-B lymphocyte origin, a PER.C6® cell line (Crucell Holland B.V., The Netherlands), or human embryonic kidney (HEK) 293 or 293T cells (ATCC® No. CRL1573).

A nucleic acid sequence encoding amino acids of any of the antibodies or antigen-binding fragments (optionally monoclonal antibodies or fragments) described herein can be introduced into a cell by transfection, transformation, or transduction.

IV. Pharmaceutical Compositions and Methods of Using Anti-*Staphylococcus aureus* Leukotoxin Antibodies The present disclosure provides compositions comprising an antibody or antigen-binding fragment thereof described herein and a pharmaceutically acceptable carrier.

The present disclosure also provides compositions comprising one or more nucleic acid sequences encoding an antibody or antigen-binding fragment thereof provided herein, or one or more vectors comprising such nucleic acid sequences.

A composition provided herein (e.g., comprising an antibody or antigen-binding fragment thereof, one or more nucleic acid sequences, or one or more vectors) can be a pharmaceutically acceptable (e.g., physiologically acceptable) composition, which comprises a carrier, such as a pharmaceutically acceptable (e.g., physiologically acceptable) carrier and the antibody or antigen-binding fragment, nucleic acid sequence(s), or vector(s).

Any suitable carrier can be used within the context of the disclosure, and such carriers are well known in the art. The choice of carrier will be determined, in part, by the particular site to which the composition may be administered and the particular method used to administer the composition. The composition optionally can be sterile. The composition can be frozen or lyophilized for storage and reconstituted in a suitable sterile carrier prior to use. The compositions can be generated in accordance with conventional techniques described in, e.g., *Remington: The Science and Practice of Pharmacy*, 21st Edition, Lippincott Williams & Wilkins, Philadelphia, Pa. (2001).

The composition desirably comprises the antibody or antigen-binding fragment in an amount that is effective to treat and/or prevent a *S. aureus* infection. To this end, the disclosed method comprises administering a therapeutically effective amount or prophylactically effective amount of a leukotoxin-binding antibody or antigen-binding fragment thereof or a composition comprising the aforementioned antibody or antigen-binding fragment thereof (including monoclonal antibodies or fragments).

The disclosure provides a method of treating or preventing a Staphylococcus aureus (S. aureus) infection in a subject (e.g., a human), which comprises administering the leukotoxin-binding antibody or antigen-binding fragment described herein to a subject in need thereof, whereupon the S. aureus infection is treated or prevented in the subject. The disclosure also provides use of the leukotoxin-binding antibody or antigen-binding fragment, described herein, or the composition comprising the antibodies or fragments thereof described herein, in the manufacture of a medicament for treating or preventing a S. aureus infection.

As discussed herein, Staphylococcus aureus is a major human pathogen that causes a wide range of clinical infections. S. aureus is a leading cause of bacteremia and infective endocarditis as well as osteoarticular, skin and soft tissue, pleuropulmonary, and device-related infections. Approximately 30% of the human population is colonized with S. aureus (Wertheim et al., Lancet Infect. Dis., 5: 751-762 (2005)). The symptoms of S. aureus skin infections include, for example, boils, cellulits, and impetigo. S. aureus also may cause food poisoning, blood poisoning (also known as bacteremia), toxic shock syndrome, and septic arthritis. The epidemiology, pathophysiology, and clinical manifestations of S. aureus infections are described in detail in, e.g., Tong et al., Clin. Microbiol. Rev., 28(3): 603-661 (2015), and the genomes of several different S. aureus strains have been sequenced (see, e.g., GenBank/EMBL Accession Nos. BX571856, BX571857, BX571858, FN433596, FN433597, FN433598, HE681097, FR821777, FR821778, FR821779, and FR821780). As discussed herein, the subject (e.g., human subject) can have diabetes.

In certain instances, a therapeutically effective amount of the leukotoxin-binding antibody or antigen-binding fragment, is an amount which inhibits S. aureus-associated sepsis, neutralizes toxins, inhibits cell lysis, inhibits multi-organ dysfunction or any combination of the foregoing, e.g., in a human.

Alternatively, the pharmacologic and/or physiologic effect may be prophylactic, i.e., the effect completely or partially prevents a disease or symptom thereof. In this respect, the disclosed method comprises administering a "prophylactically effective amount" of the leukotoxin-binding antibody or antigen-binding fragment, (including monoclonal antibodies or fragments).

Therapeutic or prophylactic efficacy can be monitored by periodic assessment of treated patients. For repeated administrations over several days or longer, depending on the condition, the treatment can be repeated until a desired suppression of disease symptoms occurs. However, other dosage regimens can be useful and are within the scope of the present disclosure. The desired dosage can be delivered by a single bolus administration of the composition, by multiple bolus administrations of the composition, or by continuous infusion administration of the composition.

The composition(s) comprising an effective amount of an antibody or antigen-binding fragment thereof described herein, nucleic acid sequence(s) encoding any of the foregoing, or vector(s) comprising the nucleic acid sequence can be administered to a subject, such as a human, using standard administration techniques, including intravenous, intraperitoneal, subcutaneous, and intramuscular administration routes. The composition may be suitable for parenteral administration. The term "parenteral," as used herein, includes intravenous, intramuscular, subcutaneous, and intraperitoneal administration. In some embodiments, the composition is administered to a subject using peripheral systemic delivery by intravenous, intraperitoneal, or subcutaneous injection.

The leukotoxin-binding antibody or antigen-binding fragment or composition comprising the same, can be administered alone or in combination with other drugs (e.g., as an adjuvant) conventionally used for treating S. aureus infections. The composition comprising the leukotoxin-binding antibody or antigen-binding fragment can be used in combination with, for example, one or more antibiotics, such as a penicillinase-resistant β-lactam antibiotic (e.g., oxacillin or flucloxacillin). Gentamicin can be used to treat serious infections, such as endocarditis. Most strains of S. aureus, however, are now resistant to penicillin, and two in 100 people carry methicillin-resistant strains of S. aureus (MRSA). MRSA infections typically are treated with vancomycin, and minor skin infections can be treated with triple antibiotic ointment.

In addition to therapeutic and prophylactic uses, any antibody or antigen-binding fragment thereof described herein can be used in diagnostic or research applications. In this respect, the leukotoxin-binding antibody or antigen-binding fragment can be used in an assay to monitor S. aureus infection in a subject. Research applications include, for example, methods that utilize the leukotoxin-binding antibody or antigen-binding fragment and a label to detect S. aureus in a sample, e.g., in a human body fluid or in a cell or tissue extract. The leukotoxin-binding antibody or antigen-binding fragment can be used with or without modification, such as covalent or non-covalent labeling with a detectable moiety. For example, the detectable moiety can be a radioisotope (e.g., $^3$H, $^{14}$C, $^{32}$P, $^{35}$S, or $^{125}$I), a fluorescent or chemiluminescent compound (e.g., fluorescein isothiocyanate, rhodamine, or luciferin), an enzyme (e.g., alkaline phosphatase, beta-galactosidase, or horseradish peroxidase), or prosthetic groups. Any method known in the art for separately conjugating an antibody or antigen-binding fragment thereof to a detectable moiety can be employed in the context of the present disclosure (see, e.g., Hunter et al., Nature, 194: 495-496 (1962); David et al., Biochemistry, 13: 1014-1021 (1974); Pain et al., J. Immunol. Meth., 40: 219-230 (1981); and Nygren, J., Histochem. And Cytochem., 30: 407-412 (1982)).

Any antibody or antigen-binding fragment thereof described herein (e.g., monoclonal antibodies or fragments), the nucleic acid sequence(s) encoding any of the foregoing, the vector(s) comprising the nucleic acid sequence(s), or the composition(s) comprising any of the foregoing, can be provided in a kit, i.e., a packaged combination of reagents in predetermined amounts with instructions for performing a diagnostic assay. If the leukotoxin-binding antibody or antigen-binding fragment is labeled with an enzyme, the kit desirably includes substrates and cofactors required by the enzyme (e.g., a substrate precursor which provides a detectable chromophore or fluorophore). In addition, other additives may be included in the kit, such as stabilizers, buffers (e.g., a blocking buffer or lysis buffer), and the like. The relative amounts of the various reagents can be varied to provide for concentrations in solution of the reagents which substantially optimize the sensitivity of the assay. The reagents may be provided as dry powders (typically lyophilized), including excipients which on dissolution will provide a reagent solution having the appropriate concentration.

The following examples further illustrate the invention but, of course, should not be construed as in any way limiting its scope.

EXAMPLE 1

The anti-leukotoxin antibody SAN481 comprises a heavy chain with the amino acid sequence of SEQ ID NO:9 and a light chain with the amino acid sequence of SEQ ID NO:10. Several sequence liabilities were identified in these sequences. For example, oxidation of heavy chain W100a (inVH-CDR3) and M256 (in the Fc domain) were observed.

In addition, a glycosylation site (NFS) in the variable heavy chain was 70% glycosylated. Two NS deamidation sites were identified in VL-CDR1, and a DG/DS isomerization site was identified in VH-CDR2. Furthermore, light sensitivity resulted in a 3.5% increase in aggregation of SAN481 upon 1 wk CWL-2kLux.

In order to achieve an improved SAN481 antibody variant, a series of sequence variants were designed and tested. The variants were designed to remove these liabilities and to increase half-life without impacting the leukotoxin neutralization activity of the antibody. (Initial attempts to remove sequence liabilities resulted in the loss of binding and neutralizing activity to LukSF. These initial attempts included mutating W102 to F, Y, A, L, I, G, and V in a construct containing the N28T mutation.) A YTE mutation was used for half-life extension, and this same mutation also removes the methionine oxidation site (residue M256) in the Fc region.

These variants were then tested for the binding and neutralizing potency against LukSF, for their photo-stability, and for their developability. The results are summarized in Table 8 below, and additional information is found in the following Examples.

TABLE 8

SAN481 and SAN481 Variants

| Variant | $IC_{50}$ (LukSF) HL-60 µg/mL | $IC_{50}$ (HIgAB) HL-60 µg/mL | Kd LukFM | Titer Mg/L | % mon. Prot. A | % mon. loss (stability) | 1 Wk Photo Stability % agg. change |
|---|---|---|---|---|---|---|---|
| SAN481 | 0.16 | 0.57 | 1.63E−10 | | 99.1% | 2.19 | 3.54% |
| SAN481-YTE | 0.15 | 0.54 | 1.48E−11 | 475 | 99.8% | −0.05 | 0.48% |
| SAN481-SY-YTE | 0.18 | 0.55 | 1.01E−10 | 834 | 99.7% | 0.18 | 0.00% |
| SAN481-T-YTE | 0.17 | 0.54 | <1.0E−12 | 800 | 99.4% | −0.02 | 0.49% |
| SAN481-TF-YTE | 0.81 | 0.44 | 1.21E−09 | 778 | 99.2% | 3.92 | Not tested |
| SAN481-SYT-YTE | 0.16 | 0.54 | 1.01E−10 | 694 | 99.5% | 0.27 | 0.18% |

"mon." = monomer
"agg." = aggregation

SAN481-SYT-YTE was selected as a particular advantageous variant in view of the fact that it had similar IC50s for LukSF, LukED, and HIgAB as SAN481, had minimal aggregation increase under light exposure, had no significant CDR deamidation and isomerization (1.1%) detected, no stability issues, no self-association, and no non-specific binding.

EXAMPLE 2

This example demonstrates that, unlike other SAN481-variants, the SAN481-SYT-YTE antibody maintains the in vitro activity of SAN481.

In vitro assays were conducted in order to evaluate the activity of SAN481 variants. In these assays, differentiated HL60 human monocytic cells (2.5e4 well/25 µl) were incubated for 2 hours at 37° C. with 50 µl of a mixture of LukSF (100 ng/ml each) or HIgAB (400 ng/ml each) and serial dilutions of each mAb mutant (25 µl) as indicated on FIG. 1. The percentage of cell viability was measured using a Cell Glo assay and calculated as follows: 100*[(OD450 cells+toxin+mAb)/(OD450 cells alone)]. The concentration of mAb required to achieve 50% inhibition of viability ($IC_{50}$) was calculated, and reported on Table 9.

TABLE 9

LukSF and HIgAB Activity of SAN481 Variants

| Variant | $IC_{50}$ for LukSF (µg/ml) | $IC_{50}$ Fold loss vs. WT | $IC_{50}$ for HIgAB (µg/ml) | $IC_{50}$ Fold loss vs. WT |
|---|---|---|---|---|
| SAN481-YTE (QD1) | 0.1499 | 0.9375 | 0.5399 | 0.9497 |
| SAN481-SY-YTE (QD2) | 0.1826 | 1.1420 | 0.5513 | 0.9697 |
| SAN481-T-YTE (QD3) | 0.1656 | 1.0356 | 0.5388 | 0.9478 |
| SAN481-TF-YTE (QD4) | 0.8109 | 5.0713 | 0.4406 | 0.7750 |
| SAN481-SYT-YTE (QD5) | 0.1617 | 1.0113 | 0.5404 | 0.9506 |
| SAN481-SYTF-YTE (QD6) | 1.369 | 8.5616 | 0.4929 | 0.8670 |
| SAN481-EG-YTE (QD11) | 0.2006 | 1.2545 | 0.503 | 0.8848 |
| SAN481-SY-QFS-YTE (QD12) | 0.1579 | 0.9875 | 0.5513 | 0.9698 |
| SAN481 | 0.1599 | | 0.5685 | |

SAN481-TF-YTE and SAN481-SYTF-YTE antibodies lost respectively 5.07 and 8.56 fold potency against LukSF as compared to SAN481. However, the SAN481-SYT-YTE antibody did not.

EXAMPLE 3

This example demonstrates that the SAN481-SYT-YTE antibody has similar in vitro leukotoxin neutralization as the SAN481 antibody.

The in vitro leukotoxin neutralization activity was tested by an assay measuring cell viability. More specifically, differentiated HL60 human monocytic cells (2.5e4 well/25 µl) were incubated for 2 hours at 37° C. with 50µl of a mixture of LukSF (100 ng/ml each), LukED (2000 ng/ml each), HlgCB (200 ng/ml each) or HIgAB (400 ng/ml each) and serial dilutions of SAN481 or SAN481_SYT-YTE (25 µl) as indicated on FIG. 2. The percentage of cell viability was measured using a Cell Glo assay and calculated as follows: 100*[(OD450 cells+toxin+mAb)/(OD450 cells alone)], and graphed on FIG. 2.

The results, shown in FIG. 2, demonstrate that SAN481-SYT-YTE and SAN481 have similar in vitro neutralization activity against all of LukSF, HIgAB, HIgBC, and LukED.

EXAMPLE 4

This example demonstrates that the SAN481-SYT-YTE demonstrates superior photostability.

The photostability of SAN481 variants was tested. In these assays, the binding affinities of mAb variants to recombinant antigens were measured by Bio-layer Interferometry on an Octet384 instrument (ForteBio, Menlo Park, Calif.). For determination the intrinsic binding affinity, antibodies at 2 µg/mL in PBS pH 7.2, 3 mg/mL BSA, 0.05% (v/v) TWEEN® 20, polysorbate 20, (1× Kinetics Buffer, ForteBio) were captured by anti-human IgG Fc biosensors (ForteBio). Following washing, association and dissociation measurements were carried out using serial dilutions of the antigen protein. The dissociation constant (KD), was deduced as the ratio of the two rate constants (koff/kon) from a non-linear fit of the data using the Octet384 software v.7.2.

The results are shown in Tables 10 and 11 below.

TABLE 10

One-Week Photostability of SAN481 Variants

| Variant | | % agg | % mon | % frag | $IC_{50}$ (LukSF) HL-60 (ug/mL) | $IC_{50}$ (HIgAB) HL-60 (ug/mL) |
|---|---|---|---|---|---|---|
| SAN481 | Light | 4.18 | 94.96 | 0.84 | | |
| SAN481 | Dark | 0.70 | 98.76 | 0.52 | 0.16 | 0.569 |
| SAN481-YTE (QD1) | Light | 0.7 | 98.46 | 0.83 | 0.233 | 0.821 |
| SAN481-YTE (QD1) | Dark | 0.22 | 99.24 | 0.53 | 0.209 | 0.704 |
| SAN481-SY-YTE (QD2) | Light | 0.46 | 99.2 | 0.32 | 0.241 | 0.736 |
| SAN481-SY-YTE (QD2) | Dark | 0.47 | 99.19 | 0.33 | 0.221 | 0.721 |
| SAN481-T-YTE (QD3) | Light | 1.32 | 98.04 | 0.62 | 0.205 | 0.624 |
| SAN481-T-YTE (QD3) | Dark | 0.83 | 98.71 | 0.44 | 0.193 | 0.707 |
| SAN481-SYT-YTE (QD5) | Light | 0.37 | 99.23 | 0.39 | 0.184 | 0.645 |
| SAN481-SYT-YTE (QD5) | Dark | 0.19 | 99.47 | 0.33 | 0.163 | 0.576 |

TABLE 11

Octet Binding Activity of Light Stressed SAN481, SAN481-YTE, and SAN481-SYT-YTE

| Antigen | Antibody/Condition | KD (M) | Kon (1/Ms) | koff (1/s) |
|---|---|---|---|---|
| LukD | SAN481 | <1.0E−12 | 3.48E+05 | <1.0E−07 |
| | SAN481-YTE (QD1)/Dark | <1.0E−12 | 2.77E+05 | <1.0E−07 |
| | SAN481-YTE (QD1)/Light | <1.0E−12 | 294200 | <1.0E−07 |
| | SAN481-SYT-YTE (QD5)/Dark | <1.0E−12 | 2.79E+05 | <1.0E−07 |
| | SAN481-SYT-YTE (QD5)/Light | <1.0E−12 | 2.63E+05 | <1.0E−07 |
| Luk F | SAN481 | 9.93E−11 | 4.02E+05 | 3.99E−05 |
| | SAN481-YTE (QD1)/Dark | 2.32E−10 | 2.83E+05 | 6.55E−05 |
| | SAN481-YTE (QD1)/Light | 2.26E−10 | 2.87E+05 | 6.47E−06 |
| | SAN481-SYT-YTE (QD5)/Dark | 1.01E−10 | 3.65E+05 | 3.69E−05 |
| | SAN481-SYT-YTE (QD5)/Light | <1.0E−12 | 2.57E+05 | <1.0E−07 |
| HIgB | SAN481 | 1.51E−10 | 2.90E+05 | 4.38E−05 |
| | SAN481-YTE (QD1)/Dark | <1.0E−12 | 2.40E+05 | <1.0E−07 |
| | SAN481-YTE (QD1)/Light | <1.0E−12 | 2.65E+05 | <1.0E−07 |
| | SAN481-SYT-YTE (QD5)/Dark | 1.91E−11 | 2.55E+05 | 4.88E−06 |
| | SAN481-SYT-YTE (QD5)/Light | <1.0E−12 | 2.44E+05 | <1.0E−07 |

The results demonstrate the superior photostability of SAN481-SYT-YTE and that there is no loss of binding for light stress samples of SAN481-SYT-YTE.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating or preventing a *Staphylococcus aureus* (*S. aureus*) infection in a subject comprising administering to the subject an antibody or antigen-binding fragment thereof that specifically binds to at least one *S. aureus* leukotoxin wherein the antibody or antigen-binding fragment comprises a variable heavy chain (VH) complementarity determining region (CDR) 1, a VH CDR2, a VH CDR3, a variable light chain (VL) CDR1, a VL CDR2, and a VL CDR3, wherein the VH CDR1, VH CDR2, VH CDR3, VL CDR1, VL CDR2, and VL CDR3 comprise sequences selected from the group consisting of: (a) SEQ ID NOs:1, 2, 3, 12, 5, and 6, respectively; (b) SEQ ID NOs:1-6, respectively; (c) SEQ ID NOs:1, 2, 17, 4, 5, and 6, respectively; (d) SEQ ID NOs: 1, 2, 17, 12, 5, and 6, respectively; and (e) SEQ ID NOs: 1, 20, 3, 4, 5, and 6, respectively.

2. The method of claim 1, wherein the *S. aureus* infection is sepsis, bacteremia, pneumonia, ICU pneumonia, a skin or soft tissue infection (SSTI), a diabetic infection of the lower limbs, a diabetic foot ulcer (DFU), a bone infection, a joint infection, a device infection, a wound infection, a surgical site infection, or osteomyelitis.

3. The method of claim 1, wherein the subject is a surgical subject.

4. The method of claim 1, wherein the *S. aureus* infection comprises antibiotic-resistant *S. aureus*.

5. The method of claim 1, wherein the subject has diabetes.

6. The method of claim 1, wherein the subject is human.

7. The method of claim 1, wherein the treating or preventing an *S. aureus* infection comprises toxin neutralization, inhibiting cell lysis, inhibiting multi-organ dysfunction, inhibiting *S. aureus*-associated sepsis, or any combination of the foregoing.

8. The method of claim 1, wherein the antibody or antigen-binding fragment thereof comprises a VH CDR1, VH CDR2, VH CDR3, VL CDR1, VL CDR2, and VL CDR3 comprising the sequences of SEQ ID NOs:1, 2, 3, 12, 5, and 6, respectively.

9. The method of claim 2, wherein the antibody or antigen-binding fragment thereof comprises a VH CDR1, VH CDR2, VH CDR3, VL CDR1, VL CDR2, and VL CDR3 comprising the sequences of SEQ ID NOs:1, 2, 3, 12, 5, and 6, respectively.

10. A method of treating or preventing a *Staphylococcus aureus* (*S. aureus*) infection in a subject comprising administering to the subject an antibody or antigen-binding fragment thereof that specifically binds to at least one *S. aureus* leukotoxin, wherein the antibody or antigen-binding fragment thereof comprises a variable heavy chain (VH) and a variable light chain (VL), wherein the VH and VL comprise sequences selected from the group consisting of: (a) SEQ ID NOs:15 and 13, respectively; (b) SEQ ID NOs:7 and 8, respectively; (c) SEQ ID NOs:7 and 13, respectively; (d) SEQ ID NOs:15 and 8, respectively; (e) SEQ ID NOs:18 and 8, respectively; (f) SEQ ID NOs:18 and 13, respectively; (g) SEQ ID NOs:21 and 8, respectively; and (h) SEQ ID NOs:23 and 13, respectively.

11. The method of claim 10, wherein the antibody or antigen-binding fragment thereof comprises a VH comprising the sequence of SEQ ID NO:15 and a VL comprising the sequence of SEQ ID NO:13.

12. The method of claim 10, wherein the *S. aureus* infection is sepsis, bacteremia, pneumonia, ICU pneumonia, a skin or soft tissue infection (SSTI), a diabetic infection of the lower limbs, a diabetic foot ulcer (DFU), a bone infection, a joint infection, a device infection, a wound infection, a surgical site infection, or osteomyelitis.

13. The method of claim 10, wherein the subject is a surgical subject.

14. The method of claim 10, wherein the subject has diabetes.

15. The method of claim 10, wherein the subject is human.

16. The method of claim 10, wherein the *S. aureus* infection comprises antibiotic-resistant *S. aureus*.

17. The method of claim 10, wherein the treating or preventing an *S. aureus* infection comprises toxin neutralization, inhibiting cell lysis, inhibiting multi-organ dysfunction, inhibiting *S. aureus*-associated sepsis, or any combination of the foregoing.

18. The method of claim 10, wherein the antibody or antigen-binding fragment thereof comprises a heavy chain and a light chain, wherein the heavy and light chains comprise sequences selected from the group consisting of: (a) SEQ ID NOs: 16 and 14, respectively; (b) SEQ ID NOs:9 and 10, respectively; (c) SEQ ID NOs:11 and 10, respectively; (d) SEQ ID NOs:11 and 14, respectively; (e) SEQ ID NOs:16 and 10, respectively; (f) SEQ ID NOs:19 and 10, respectively; (g) SEQ ID NOs:19 and 14, respectively; (h) SEQ ID NOs:22 and 10, respectively; and (i) SEQ ID NOs:24 and 14, respectively.

19. The method of claim 10, wherein the antibody or antigen-binding fragment thereof comprises a heavy chain comprising the sequence of SEQ ID NO:16 and a light chain comprising the sequence of SEQ ID NO:14.

20. The method of claim 17, wherein the antibody or antigen-binding fragment thereof comprises a heavy chain comprising the sequence of SEQ ID NO:16 and a light chain comprising the sequence of SEQ ID NO:14.

* * * * *

SEQUENCE LISTING

```
<160> NUMBER OF SEQ ID NOS: 28

<210> SEQ ID NO 1
<211> LENGTH: 5
<212> TYPE: PRT
<213> ORGANISM: Artificial Sequence
<220> FEATURE:
<223> OTHER INFORMATION: SAN481 VH CDR1

<400> SEQUENCE: 1

Thr Tyr Ala Met His
1               5

<210> SEQ ID NO 2
<211> LENGTH: 17
<212> TYPE: PRT
<213> ORGANISM: Artificial Sequence
<220> FEATURE:
<223> OTHER INFORMATION: SAN481 VH CDR2

<400> SEQUENCE: 2

Val Thr Ser Phe Asp Gly Ser Asn Glu Tyr Tyr Ile Asp Ser Val Lys
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: SAN481 VH CDR3

<400> SEQUENCE: 3

Asp Glu Tyr Thr Gly Gly Trp Tyr Ser Val Gly Tyr
1               5                   10

<210> SEQ ID NO 4
<211> LENGTH: 13
<212> TYPE: PRT
<213> ORGANISM: Artificial Sequence
<220> FEATURE:
<223> OTHER INFORMATION: SAN 481 VL CDR1

<400> SEQUENCE: 4

Ser Gly Asn Ser Tyr Asn Ile Gly Ser Asn Ser Val Tyr
1               5                   10

<210> SEQ ID NO 5
<211> LENGTH: 7
```

```
<212> TYPE: PRT
<213> ORGANISM: Artificial Sequence
<220> FEATURE:
<223> OTHER INFORMATION: SAN481 VL CDR2

<400> SEQUENCE: 5

Arg Ser Ile Gln Arg Pro Ser
1               5

<210> SEQ ID NO 6
<211> LENGTH: 11
<212> TYPE: PRT
<213> ORGANISM: Artificial Sequence
<220> FEATURE:
<223> OTHER INFORMATION: SAN481 VL CDR3

<400> SEQUENCE: 6

Ala Ala Trp Asp Asp Ser Leu Arg Ala Trp Val
1               5                   10

<210> SEQ ID NO 7
<211> LENGTH: 121
<212> TYPE: PRT
<213> ORGANISM: Artificial Sequence
<220> FEATURE:
<223> OTHER INFORMATION: SAN481 VH

<400> SEQUENCE: 7

Gln Leu Gln Leu Val Glu Ser Gly Gly Gly Ala Val Gln Pro Gly Arg
1               5                   10                  15

Ser Leu Lys Leu Ser Cys Ala Ala Ser Gly Phe Asn Phe Ser Thr Tyr
            20                  25                  30

Ala Met His Trp Val Arg Gln Ala Pro Gly Arg Gly Leu Glu Trp Val
        35                  40                  45

Ala Val Thr Ser Phe Asp Gly Ser Asn Glu Tyr Tyr Ile Asp Ser Val
    50                  55                  60

Lys Gly Arg Phe Thr Ile Ser Arg Asp Asn Thr Lys Asn Thr Leu Tyr
65                  70                  75                  80

Leu Gln Met Thr Gly Leu Arg Val Glu Asp Thr Ala Leu Tyr Phe Cys
                85                  90                  95

Ala Arg Asp Glu Tyr Thr Gly Gly Trp Tyr Ser Val Gly Tyr Trp Gly
            100                 105                 110

Gln Gly Thr Leu Val Thr Val Ser Ser
        115                 120

<210> SEQ ID NO 8
<211> LENGTH: 110
<212> TYPE: PRT
<213> ORGANISM: Artificial Sequence
<220> FEATURE:
<223> OTHER INFORMATION: SAN481 VL

<400> SEQUENCE: 8

Gln Ser Val Leu Thr Gln Pro Pro Ser Ala Ser Gly Thr Pro Gly Gln
1               5                   10                  15

Arg Val Thr Ile Ser Cys Ser Gly Asn Ser Tyr Asn Ile Gly Ser Asn
            20                  25                  30

Ser Val Tyr Trp Tyr Gln Gln Phe Pro Gly Thr Ala Pro Lys Leu Leu
        35                  40                  45

Ile Ser Arg Ser Ile Gln Arg Pro Ser Gly Val Pro Asp Arg Phe Ser
    50                  55                  60
```

```
Gly Ser Lys Ser Val Thr Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Arg Ala Trp Val Phe Gly Gly Gly Thr Lys Leu Thr Val Leu
            100                 105                 110

<210> SEQ ID NO 9
<211> LENGTH: 451
<212> TYPE: PRT
<213> ORGANISM: Artificial Sequence
<220> FEATURE:
<223> OTHER INFORMATION: SAN481 Heavy Chain

<400> SEQUENCE: 9

Gln Leu Gln Leu Val Glu Ser Gly Gly Gly Ala Val Gln Pro Gly Arg
 1               5                  10                  15

Ser Leu Lys Leu Ser Cys Ala Ala Ser Gly Phe Asn Phe Ser Thr Tyr
                20                  25                  30

Ala Met His Trp Val Arg Gln Ala Pro Gly Arg Gly Leu Glu Trp Val
             35                  40                  45

Ala Val Thr Ser Phe Asp Gly Ser Asn Glu Tyr Tyr Ile Asp Ser Val
 50                  55                  60

Lys Gly Arg Phe Thr Ile Ser Arg Asp Asn Thr Lys Asn Thr Leu Tyr
 65                  70                  75                  80

Leu Gln Met Thr Gly Leu Arg Val Glu Asp Thr Ala Leu Tyr Phe Cys
                 85                  90                  95

Ala Arg Asp Glu Tyr Thr Gly Gly Trp Tyr Ser Val Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320
```

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 10
<211> LENGTH: 216
<212> TYPE: PRT
<213> ORGANISM: Artificial Sequence
<220> FEATURE:
<223> OTHER INFORMATION: SAN481 Light Chain

<400> SEQUENCE: 10

Gln Ser Val Leu Thr Gln Pro Pro Ser Ala Ser Gly Thr Pro Gly Gln
1               5                   10                  15

Arg Val Thr Ile Ser Cys Ser Gly Asn Ser Tyr Asn Ile Gly Ser Asn
            20                  25                  30

Ser Val Tyr Trp Tyr Gln Gln Phe Pro Gly Thr Ala Pro Lys Leu Leu
        35                  40                  45

Ile Ser Arg Ser Ile Gln Arg Pro Ser Gly Val Pro Asp Arg Phe Ser
50                  55                  60

Gly Ser Lys Ser Val Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Arg Ala Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 11
<211> LENGTH: 451
<212> TYPE: PRT
<213> ORGANISM: Artificial Sequence
<220> FEATURE:
<223> OTHER INFORMATION: SAN481-YTE Heavy Chain

<400> SEQUENCE: 11

```
Gln Leu Gln Leu Val Glu Ser Gly Gly Gly Ala Val Gln Pro Gly Arg
1               5                   10                  15

Ser Leu Lys Leu Ser Cys Ala Ala Ser Gly Phe Asn Phe Ser Thr Tyr
            20                  25                  30

Ala Met His Trp Val Arg Gln Ala Pro Gly Arg Gly Leu Glu Trp Val
        35                  40                  45

Ala Val Thr Ser Phe Asp Gly Ser Asn Glu Tyr Tyr Ile Asp Ser Val
    50                  55                  60

Lys Gly Arg Phe Thr Ile Ser Arg Asp Asn Thr Lys Asn Thr Leu Tyr
65                  70                  75                  80

Leu Gln Met Thr Gly Leu Arg Val Glu Asp Thr Ala Leu Tyr Phe Cys
                85                  90                  95

Ala Arg Asp Glu Tyr Thr Gly Gly Trp Tyr Ser Val Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Tyr
                245                 250                 255

Ile Thr Arg Glu Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365
```

```
Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 12
<211> LENGTH: 13
<212> TYPE: PRT
<213> ORGANISM: Artificial Sequence
<220> FEATURE:
<223> OTHER INFORMATION: SAN481-SY VL CDR1

<400> SEQUENCE: 12

Ser Gly Ser Ser Tyr Asn Ile Gly Ser Asn Tyr Val Tyr
1               5                   10

<210> SEQ ID NO 13
<211> LENGTH: 110
<212> TYPE: PRT
<213> ORGANISM: Artificial Sequence
<220> FEATURE:
<223> OTHER INFORMATION: SAN481-SY VL

<400> SEQUENCE: 13

Gln Ser Val Leu Thr Gln Pro Pro Ser Ala Ser Gly Thr Pro Gly Gln
1               5                   10                  15

Arg Val Thr Ile Ser Cys Ser Gly Ser Ser Tyr Asn Ile Gly Ser Asn
            20                  25                  30

Tyr Val Tyr Trp Tyr Gln Gln Phe Pro Gly Thr Ala Pro Lys Leu Leu
        35                  40                  45

Ile Ser Arg Ser Ile Gln Arg Pro Ser Gly Val Pro Asp Arg Phe Ser
    50                  55                  60

Gly Ser Lys Ser Val Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Arg Ala Trp Val Phe Gly Gly Gly Thr Lys Leu Thr Val Leu
                100                 105                 110

<210> SEQ ID NO 14
<211> LENGTH: 216
<212> TYPE: PRT
<213> ORGANISM: Artificial Sequence
<220> FEATURE:
<223> OTHER INFORMATION: SAN481-SY Light Chain

<400> SEQUENCE: 14

Gln Ser Val Leu Thr Gln Pro Pro Ser Ala Ser Gly Thr Pro Gly Gln
1               5                   10                  15

Arg Val Thr Ile Ser Cys Ser Gly Ser Ser Tyr Asn Ile Gly Ser Asn
            20                  25                  30

Tyr Val Tyr Trp Tyr Gln Gln Phe Pro Gly Thr Ala Pro Lys Leu Leu
```

```
                    35                  40                  45
Ile Ser Arg Ser Ile Gln Arg Pro Ser Gly Val Pro Asp Arg Phe Ser
             50                  55                  60
Gly Ser Lys Ser Val Thr Ser Ala Ser Leu Ala Ile Ser Gly Leu Arg
 65                  70                  75                  80
Ser Glu Asp Glu Ala Asp Tyr Tyr Cys Ala Trp Asp Asp Ser Leu
                 85                  90                  95
Arg Ala Trp Val Phe Gly Gly Gly Thr Lys Leu Thr Val Leu Gly Gln
            100                 105                 110
Pro Lys Ala Ala Pro Ser Val Thr Leu Phe Pro Pro Ser Ser Glu Glu
        115                 120                 125
Leu Gln Ala Asn Lys Ala Thr Leu Val Cys Leu Ile Ser Asp Phe Tyr
    130                 135                 140
Pro Gly Ala Val Thr Val Ala Trp Lys Ala Asp Ser Ser Pro Val Lys
145                 150                 155                 160
Ala Gly Val Glu Thr Thr Thr Pro Ser Lys Gln Ser Asn Asn Lys Tyr
                165                 170                 175
Ala Ala Ser Ser Tyr Leu Ser Leu Thr Pro Glu Gln Trp Lys Ser His
            180                 185                 190
Arg Ser Tyr Ser Cys Gln Val Thr His Glu Gly Ser Thr Val Glu Lys
        195                 200                 205
Thr Val Ala Pro Thr Glu Cys Ser
    210                 215

<210> SEQ ID NO 15
<211> LENGTH: 121
<212> TYPE: PRT
<213> ORGANISM: Artificial Sequence
<220> FEATURE:
<223> OTHER INFORMATION: SAN481-T VH

<400> SEQUENCE: 15

Gln Leu Gln Leu Val Glu Ser Gly Gly Gly Ala Val Gln Pro Gly Arg
 1               5                  10                  15
Ser Leu Lys Leu Ser Cys Ala Ala Ser Gly Phe Thr Phe Ser Thr Tyr
                20                  25                  30
Ala Met His Trp Val Arg Gln Ala Pro Gly Arg Gly Leu Glu Trp Val
            35                  40                  45
Ala Val Thr Ser Phe Asp Gly Ser Asn Glu Tyr Tyr Ile Asp Ser Val
        50                  55                  60
Lys Gly Arg Phe Thr Ile Ser Arg Asp Asn Lys Asn Thr Leu Tyr
 65                  70                  75                  80
Leu Gln Met Thr Gly Leu Arg Val Glu Asp Thr Ala Leu Tyr Phe Cys
                 85                  90                  95
Ala Arg Asp Glu Tyr Thr Gly Gly Trp Tyr Ser Val Gly Tyr Trp Gly
            100                 105                 110
Gln Gly Thr Leu Val Thr Val Ser Ser
        115                 120

<210> SEQ ID NO 16
<211> LENGTH: 451
<212> TYPE: PRT
<213> ORGANISM: Artificial Sequence
<220> FEATURE:
<223> OTHER INFORMATION: SAN481-T-YTE Heavy Chain

<400> SEQUENCE: 16
```

-continued

Gln Leu Gln Leu Val Glu Ser Gly Gly Gly Ala Val Gln Pro Gly Arg
1               5                   10                  15

Ser Leu Lys Leu Ser Cys Ala Ala Ser Gly Phe Thr Phe Ser Thr Tyr
            20                  25                  30

Ala Met His Trp Val Arg Gln Ala Pro Gly Arg Gly Leu Glu Trp Val
        35                  40                  45

Ala Val Thr Ser Phe Asp Gly Ser Asn Glu Tyr Tyr Ile Asp Ser Val
    50                  55                  60

Lys Gly Arg Phe Thr Ile Ser Arg Asp Asn Lys Asn Thr Leu Tyr
65                  70                  75                  80

Leu Gln Met Thr Gly Leu Arg Val Glu Asp Thr Ala Leu Tyr Phe Cys
            85                  90                  95

Ala Arg Asp Glu Tyr Thr Gly Gly Trp Tyr Ser Val Gly Tyr Trp Gly
        100                 105                 110

Gln Gly Thr Leu Val Thr Val Ser Ser Ala Ser Thr Lys Gly Pro Ser
    115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Tyr
            245                 250                 255

Ile Thr Arg Glu Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Glu Glu Met Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met

-continued

```
                420                 425                 430

His Glu Ala Leu His Asn His Tyr Thr Gln Lys Ser Leu Ser Leu Ser
            435                 440                 445

Pro Gly Lys
        450

<210> SEQ ID NO 17
<211> LENGTH: 12
<212> TYPE: PRT
<213> ORGANISM: Artificial Sequence
<220> FEATURE:
<223> OTHER INFORMATION: SAN481-TF VH CDR3

<400> SEQUENCE: 17

Asp Glu Tyr Thr Gly Gly Phe Tyr Ser Val Gly Tyr
1               5                   10

<210> SEQ ID NO 18
<211> LENGTH: 121
<212> TYPE: PRT
<213> ORGANISM: Artificial Sequence
<220> FEATURE:
<223> OTHER INFORMATION: SAN481-TF VH

<400> SEQUENCE: 18

Gln Leu Gln Leu Val Glu Ser Gly Gly Gly Ala Val Gln Pro Gly Arg
1               5                   10                  15

Ser Leu Lys Leu Ser Cys Ala Ala Ser Gly Phe Thr Phe Ser Thr Tyr
            20                  25                  30

Ala Met His Trp Val Arg Gln Ala Pro Gly Arg Gly Leu Glu Trp Val
        35                  40                  45

Ala Val Thr Ser Phe Asp Gly Ser Asn Glu Tyr Tyr Ile Asp Ser Val
    50                  55                  60

Lys Gly Arg Phe Thr Ile Ser Arg Asp Asn Thr Lys Asn Thr Leu Tyr
65                  70                  75                  80

Leu Gln Met Thr Gly Leu Arg Val Glu Asp Thr Ala Leu Tyr Phe Cys
                85                  90                  95

Ala Arg Asp Glu Tyr Thr Gly Gly Phe Tyr Ser Val Gly Tyr Trp Gly
            100                 105                 110

Gln Gly Thr Leu Val Thr Val Ser Ser
        115                 120

<210> SEQ ID NO 19
<211> LENGTH: 451
<212> TYPE: PRT
<213> ORGANISM: Artificial Sequence
<220> FEATURE:
<223> OTHER INFORMATION: SAN481-TF-YTE Heavy Chain

<400> SEQUENCE: 19

Gln Leu Gln Leu Val Glu Ser Gly Gly Gly Ala Val Gln Pro Gly Arg
1               5                   10                  15

Ser Leu Lys Leu Ser Cys Ala Ala Ser Gly Phe Thr Phe Ser Thr Tyr
            20                  25                  30

Ala Met His Trp Val Arg Gln Ala Pro Gly Arg Gly Leu Glu Trp Val
        35                  40                  45

Ala Val Thr Ser Phe Asp Gly Ser Asn Glu Tyr Tyr Ile Asp Ser Val
    50                  55                  60

Lys Gly Arg Phe Thr Ile Ser Arg Asp Asn Thr Lys Asn Thr Leu Tyr
65                  70                  75                  80
```

```
Leu Gln Met Thr Gly Leu Arg Val Glu Asp Thr Ala Leu Tyr Phe Cys
                85                  90                  95

Ala Arg Asp Glu Tyr Thr Gly Gly Phe Tyr Ser Val Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Tyr
                245                 250                 255

Ile Thr Arg Glu Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 20
<211> LENGTH: 17
<212> TYPE: PRT
<213> ORGANISM: Artificial Sequence
<220> FEATURE:
```

<223> OTHER INFORMATION: SAN481-EG VH CDR2

<400> SEQUENCE: 20

Val Thr Ser Phe Glu Gly Ser Asn Glu Tyr Tyr Ile Asp Ser Val Lys
1               5                   10                  15

Gly

<210> SEQ ID NO 21
<211> LENGTH: 121
<212> TYPE: PRT
<213> ORGANISM: Artificial Sequence
<220> FEATURE:
<223> OTHER INFORMATION: SAN481-EG VH

<400> SEQUENCE: 21

Gln Leu Gln Leu Val Glu Ser Gly Gly Gly Ala Val Gln Pro Gly Arg
1               5                   10                  15

Ser Leu Lys Leu Ser Cys Ala Ala Ser Gly Phe Asn Phe Ser Thr Tyr
            20                  25                  30

Ala Met His Trp Val Arg Gln Ala Pro Gly Arg Gly Leu Glu Trp Val
        35                  40                  45

Ala Val Thr Ser Phe Glu Gly Ser Asn Glu Tyr Tyr Ile Asp Ser Val
    50                  55                  60

Lys Gly Arg Phe Thr Ile Ser Arg Asp Asn Thr Lys Asn Thr Leu Tyr
65                  70                  75                  80

Leu Gln Met Thr Gly Leu Arg Val Glu Asp Thr Ala Leu Tyr Phe Cys
                85                  90                  95

Ala Arg Asp Glu Tyr Thr Gly Gly Trp Tyr Ser Val Gly Tyr Trp Gly
            100                 105                 110

Gln Gly Thr Leu Val Thr Val Ser Ser
        115                 120

<210> SEQ ID NO 22
<211> LENGTH: 451
<212> TYPE: PRT
<213> ORGANISM: Artificial Sequence
<220> FEATURE:
<223> OTHER INFORMATION: SAN481-EG-YTE Heavy Chain

<400> SEQUENCE: 22

Gln Leu Gln Leu Val Glu Ser Gly Gly Gly Ala Val Gln Pro Gly Arg
1               5                   10                  15

Ser Leu Lys Leu Ser Cys Ala Ala Ser Gly Phe Asn Phe Ser Thr Tyr
            20                  25                  30

Ala Met His Trp Val Arg Gln Ala Pro Gly Arg Gly Leu Glu Trp Val
        35                  40                  45

Ala Val Thr Ser Phe Glu Gly Ser Asn Glu Tyr Tyr Ile Asp Ser Val
    50                  55                  60

Lys Gly Arg Phe Thr Ile Ser Arg Asp Asn Thr Lys Asn Thr Leu Tyr
65                  70                  75                  80

Leu Gln Met Thr Gly Leu Arg Val Glu Asp Thr Ala Leu Tyr Phe Cys
                85                  90                  95

Ala Arg Asp Glu Tyr Thr Gly Gly Trp Tyr Ser Val Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Tyr
                245                 250                 255

Ile Thr Arg Glu Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 23
<211> LENGTH: 121
<212> TYPE: PRT
<213> ORGANISM: Artificial Sequence
<220> FEATURE:
<223> OTHER INFORMATION: SAN481-QFS VH

<400> SEQUENCE: 23

Gln Leu Gln Leu Val Glu Ser Gly Gly Gly Ala Val Gln Pro Gly Arg
1               5                   10                  15

Ser Leu Lys Leu Ser Cys Ala Ala Ser Gly Phe Gln Phe Ser Thr Tyr
            20                  25                  30

Ala Met His Trp Val Arg Gln Ala Pro Gly Arg Gly Leu Glu Trp Val
        35                  40                  45
```

Ala Val Thr Ser Phe Asp Gly Ser Asn Glu Tyr Tyr Ile Asp Ser Val
            50                      55                      60

Lys Gly Arg Phe Thr Ile Ser Arg Asp Asn Thr Lys Asn Thr Leu Tyr
 65                      70                      75                      80

Leu Gln Met Thr Gly Leu Arg Val Glu Asp Thr Ala Leu Tyr Phe Cys
                        85                      90                      95

Ala Arg Asp Glu Tyr Thr Gly Gly Trp Tyr Ser Val Gly Tyr Trp Gly
                100                     105                     110

Gln Gly Thr Leu Val Thr Val Ser Ser
                115                     120

<210> SEQ ID NO 24
<211> LENGTH: 451
<212> TYPE: PRT
<213> ORGANISM: Artificial Sequence
<220> FEATURE:
<223> OTHER INFORMATION: SAN481-QFS-YTE Heavy Chain

<400> SEQUENCE: 24

Gln Leu Gln Leu Val Glu Ser Gly Gly Gly Ala Val Gln Pro Gly Arg
 1                       5                      10                      15

Ser Leu Lys Leu Ser Cys Ala Ala Ser Gly Phe Gln Phe Ser Thr Tyr
                 20                      25                      30

Ala Met His Trp Val Arg Gln Ala Pro Gly Arg Gly Leu Glu Trp Val
                 35                      40                      45

Ala Val Thr Ser Phe Asp Gly Ser Asn Glu Tyr Tyr Ile Asp Ser Val
            50                      55                      60

Lys Gly Arg Phe Thr Ile Ser Arg Asp Asn Thr Lys Asn Thr Leu Tyr
 65                      70                      75                      80

Leu Gln Met Thr Gly Leu Arg Val Glu Asp Thr Ala Leu Tyr Phe Cys
                        85                      90                      95

Ala Arg Asp Glu Tyr Thr Gly Gly Trp Tyr Ser Val Gly Tyr Trp Gly
                100                     105                     110

Gln Gly Thr Leu Val Thr Val Ser Ser Ala Ser Thr Lys Gly Pro Ser
                115                     120                     125

Val Phe Pro Leu Ala Pro Ser Ser Lys Ser Thr Ser Gly Gly Thr Ala
    130                     135                     140

Ala Leu Gly Cys Leu Val Lys Asp Tyr Phe Pro Glu Pro Val Thr Val
145                     150                     155                     160

Ser Trp Asn Ser Gly Ala Leu Thr Ser Gly Val His Thr Phe Pro Ala
                165                     170                     175

Val Leu Gln Ser Ser Gly Leu Tyr Ser Leu Ser Ser Val Val Thr Val
                180                     185                     190

Pro Ser Ser Ser Leu Gly Thr Gln Thr Tyr Ile Cys Asn Val Asn His
                195                     200                     205

Lys Pro Ser Asn Thr Lys Val Asp Lys Arg Val Glu Pro Lys Ser Cys
    210                     215                     220

Asp Lys Thr His Thr Cys Pro Pro Cys Pro Ala Pro Glu Leu Leu Gly
225                     230                     235                     240

Gly Pro Ser Val Phe Leu Phe Pro Pro Lys Pro Lys Asp Thr Leu Tyr
                245                     250                     255

Ile Thr Arg Glu Pro Glu Val Thr Cys Val Val Val Asp Val Ser His
                260                     265                     270

Glu Asp Pro Glu Val Lys Phe Asn Trp Tyr Val Asp Gly Val Glu Val
                275                     280                     285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 25
<211> LENGTH: 302
<212> TYPE: PRT
<213> ORGANISM: Artificial Sequence
<220> FEATURE:
<223> OTHER INFORMATION: LukF

<400> SEQUENCE: 25

Gly Ala Gln His Ile Thr Pro Val Ser Glu Lys Lys Val Asp Asp Lys
1               5                   10                  15

Ile Thr Leu Tyr Lys Thr Thr Ala Thr Ser Asp Ser Asp Lys Leu Lys
            20                  25                  30

Ile Ser Gln Ile Leu Thr Phe Asn Phe Ile Lys Asp Lys Ser Tyr Asp
        35                  40                  45

Lys Asp Thr Leu Ile Leu Lys Ala Ala Gly Asn Ile Tyr Ser Gly Tyr
    50                  55                  60

Thr Lys Pro Asn Pro Lys Asp Thr Ile Ser Ser Gln Phe Tyr Trp Gly
65                  70                  75                  80

Ser Lys Tyr Asn Ile Ser Ile Asn Ser Asp Ser Asn Asp Ser Val Asn
                85                  90                  95

Val Val Asp Tyr Ala Pro Lys Asn Gln Asn Glu Glu Phe Gln Val Gln
                100                 105                 110

Gln Thr Val Gly Tyr Ser Tyr Gly Gly Asp Ile Asn Ile Ser Asn Gly
            115                 120                 125

Leu Ser Gly Gly Gly Asn Gly Ser Lys Ser Phe Ser Glu Thr Ile Asn
    130                 135                 140

Tyr Lys Gln Glu Ser Tyr Arg Thr Ser Leu Asp Lys Arg Thr Asn Phe
145                 150                 155                 160

Lys Lys Ile Gly Trp Asp Val Glu Ala His Lys Ile Met Asn Asn Gly
                165                 170                 175

Trp Gly Pro Tyr Gly Arg Asp Ser Tyr His Ser Thr Tyr Gly Asn Glu
            180                 185                 190

```
Met Phe Leu Gly Ser Arg Gln Ser Asn Leu Asn Ala Gly Gln Asn Phe
            195                 200                 205

Leu Glu Tyr His Lys Met Pro Val Leu Ser Arg Gly Asn Phe Asn Pro
210                 215                 220

Glu Phe Ile Gly Val Leu Ser Arg Lys Gln Asn Ala Ala Lys Lys Ser
225                 230                 235                 240

Lys Ile Thr Val Thr Tyr Gln Arg Glu Met Asp Arg Tyr Thr Asn Phe
            245                 250                 255

Trp Asn Gln Leu His Trp Ile Gly Asn Asn Tyr Lys Asp Glu Asn Arg
                260                 265                 270

Ala Thr His Thr Ser Ile Tyr Glu Val Asp Trp Glu Asn His Thr Val
            275                 280                 285

Lys Leu Ile Asp Thr Gln Ser Lys Glu Lys Asn Pro Met Ser
290                 295                 300
```

<210> SEQ ID NO 26
<211> LENGTH: 302
<212> TYPE: PRT
<213> ORGANISM: Artificial Sequence
<220> FEATURE:
<223> OTHER INFORMATION: LukD

<400> SEQUENCE: 26

```
Gly Ala Gln His Ile Thr Pro Val Ser Glu Lys Lys Val Asp Asp Lys
1               5                   10                  15

Ile Thr Leu Tyr Lys Thr Thr Ala Thr Ser Asp Asn Asp Lys Leu Asn
            20                  25                  30

Ile Ser Gln Ile Leu Thr Phe Asn Phe Ile Lys Asp Lys Ser Tyr Asp
        35                  40                  45

Lys Asp Thr Leu Val Leu Lys Ala Ala Gly Asn Ile Asn Ser Gly Tyr
50                  55                  60

Lys Lys Pro Asn Pro Lys Asp Tyr Asn Tyr Ser Gln Phe Tyr Trp Gly
65                  70                  75                  80

Gly Lys Tyr Asn Val Ser Val Ser Ser Glu Ser Asn Asp Ala Val Asn
                85                  90                  95

Val Val Asp Tyr Ala Pro Lys Asn Gln Asn Glu Glu Phe Gln Val Gln
            100                 105                 110

Gln Thr Leu Gly Tyr Ser Tyr Gly Gly Asp Ile Asn Ile Ser Asn Gly
        115                 120                 125

Leu Ser Gly Gly Leu Asn Gly Ser Lys Ser Phe Ser Glu Thr Ile Asn
130                 135                 140

Tyr Lys Gln Glu Ser Tyr Arg Thr Thr Ile Asp Arg Lys Thr Asn His
145                 150                 155                 160

Lys Ser Ile Gly Trp Gly Val Glu Ala His Lys Ile Met Asn Asn Gly
                165                 170                 175

Trp Gly Pro Tyr Gly Arg Asp Ser Tyr Asp Pro Thr Tyr Gly Asn Glu
            180                 185                 190

Leu Phe Leu Gly Gly Arg Gln Ser Ser Ser Asn Ala Gly Gln Asn Phe
        195                 200                 205

Leu Pro Thr His Gln Met Pro Leu Leu Ala Arg Gly Asn Phe Asn Pro
210                 215                 220

Glu Phe Ile Ser Val Leu Ser His Lys Gln Asn Asp Thr Lys Lys Ser
225                 230                 235                 240

Lys Ile Lys Val Thr Tyr Gln Arg Glu Met Asp Arg Tyr Thr Asn Gln
                245                 250                 255
```

```
Trp Asn Arg Leu His Trp Val Gly Asn Asn Tyr Lys Asn Gln Asn Thr
            260                 265                 270

Val Thr Phe Thr Ser Thr Tyr Glu Val Asp Trp Gln Asn His Thr Val
275                 280                 285

Lys Leu Ile Gly Thr Asp Ser Lys Glu Thr Asn Pro Gly Val
    290                 295                 300
```

<210> SEQ ID NO 27
<211> LENGTH: 300
<212> TYPE: PRT
<213> ORGANISM: Artificial Sequence
<220> FEATURE:
<223> OTHER INFORMATION: HIgB

<400> SEQUENCE: 27

```
Gly Glu Gly Lys Ile Thr Pro Val Ser Val Lys Val Asp Asp Lys
1               5                   10                  15

Val Thr Leu Tyr Lys Thr Thr Ala Thr Ala Asp Ser Asp Lys Phe Lys
            20                  25                  30

Ile Ser Gln Ile Leu Thr Phe Asn Phe Ile Lys Asp Lys Ser Tyr Asp
        35                  40                  45

Lys Asp Thr Leu Val Leu Lys Ala Thr Gly Asn Ile Asn Ser Gly Phe
    50                  55                  60

Val Lys Pro Asn Pro Asn Asp Tyr Asp Phe Ser Lys Leu Tyr Trp Gly
65                  70                  75                  80

Ala Lys Tyr Asn Val Ser Ile Ser Ser Gln Ser Asn Asp Ser Val Asn
                85                  90                  95

Val Val Asp Tyr Ala Pro Lys Asn Gln Asn Glu Glu Phe Gln Val Gln
            100                 105                 110

Asn Thr Leu Gly Tyr Thr Phe Gly Gly Asp Ile Ser Ile Ser Asn Gly
        115                 120                 125

Leu Ser Gly Gly Leu Asn Gly Asn Thr Ala Phe Ser Glu Thr Ile Asn
    130                 135                 140

Tyr Lys Gln Glu Ser Tyr Arg Thr Thr Leu Ser Arg Asn Thr Asn Tyr
145                 150                 155                 160

Lys Asn Val Gly Trp Gly Val Glu Ala His Lys Ile Met Asn Asn Gly
                165                 170                 175

Trp Gly Pro Tyr Gly Arg Asp Ser Phe His Pro Thr Tyr Gly Asn Glu
            180                 185                 190

Leu Phe Leu Ala Gly Arg Gln Ser Ser Ala Tyr Ala Gly Gln Asn Phe
        195                 200                 205

Ile Ala Gln His Gln Met Pro Leu Leu Ser Arg Ser Asn Phe Asn Pro
    210                 215                 220

Glu Phe Leu Ser Val Leu Ser His Arg Gln Asp Gly Ala Lys Lys Ser
225                 230                 235                 240

Lys Ile Thr Val Thr Tyr Gln Arg Glu Met Asp Leu Tyr Gln Ile Arg
                245                 250                 255

Trp Asn Gly Phe Tyr Trp Ala Gly Ala Asn Tyr Lys Asn Phe Lys Thr
            260                 265                 270

Arg Thr Phe Lys Ser Thr Tyr Glu Ile Asp Trp Glu Asn His Lys Val
        275                 280                 285

Lys Leu Leu Asp Thr Lys Glu Thr Glu Asn Asn Lys
    290                 295                 300
```

<210> SEQ ID NO 28

<211> LENGTH: 451
<212> TYPE: PRT
<213> ORGANISM: Artificial Sequence
<220> FEATURE:
<223> OTHER INFORMATION: SAN481-T Heavy Chain

<400> SEQUENCE: 28

```
Gln Leu Gln Leu Val Glu Ser Gly Gly Gly Ala Val Gln Pro Gly Arg
1               5                   10                  15

Ser Leu Lys Leu Ser Cys Ala Ala Ser Gly Phe Thr Phe Ser Thr Tyr
            20                  25                  30

Ala Met His Trp Val Arg Gln Ala Pro Gly Arg Gly Leu Glu Trp Val
        35                  40                  45

Ala Val Thr Ser Phe Asp Gly Ser Asn Glu Tyr Tyr Ile Asp Ser Val
    50                  55                  60

Lys Gly Arg Phe Thr Ile Ser Arg Asp Asn Thr Lys Asn Thr Leu Tyr
65                  70                  75                  80

Leu Gln Met Thr Gly Leu Arg Val Glu Asp Thr Ala Leu Tyr Phe Cys
                85                  90                  95

Ala Arg Asp Glu Tyr Thr Gly Gly Trp Tyr Ser Val Gly Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380
```

```
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450
```